United States Patent
Yamakawa

(10) Patent No.: US 10,806,385 B2
(45) Date of Patent: Oct. 20, 2020

(54) DEVICE FOR MEASURING CONCENTRATION OF SUBSTANCE IN BLOOD, AND METHOD FOR MEASURING CONCENTRATION OF SUBSTANCE IN BLOOD

(71) Applicant: National Institutes for Quantum and Radiological Science and Technology, Chiba (JP)

(72) Inventor: Koichi Yamakawa, Kyoto (JP)

(73) Assignee: National Institutes for Quantum and Radiological Science and Technology, Chiba (JP)

( * ) Notice: Subject to any disclaimer, the term of this patent is extended or adjusted under 35 U.S.C. 154(b) by 322 days.

(21) Appl. No.: 15/545,661

(22) PCT Filed: Jan. 19, 2016

(86) PCT No.: PCT/JP2016/051339
§ 371 (c)(1),
(2) Date: Jul. 21, 2017

(87) PCT Pub. No.: WO2016/117520
PCT Pub. Date: Jul. 28, 2016

(65) Prior Publication Data
US 2018/0000386 A1     Jan. 4, 2018

(30) Foreign Application Priority Data
Jan. 21, 2015   (JP) ................. 2015-009504

(51) Int. Cl.
*A61B 5/1455*     (2006.01)
*G01N 21/55*      (2014.01)
(Continued)

(52) U.S. Cl.
CPC ........ *A61B 5/1455* (2013.01); *A61B 5/14532* (2013.01); *A61B 5/14546* (2013.01);
(Continued)

(58) Field of Classification Search
None
See application file for complete search history.

(56) References Cited

U.S. PATENT DOCUMENTS 4,169,676 A * 10/1979 Kaiser .................. G01N 21/552
356/39
4,259,963 A    4/1981 Huch
(Continued)

FOREIGN PATENT DOCUMENTS

CN    1204496 A    1/1999
CN    101263388 A  9/2008
(Continued)

OTHER PUBLICATIONS

European Patent Office. Office action of foreign counterpart, dated Oct. 16, 2019.
(Continued)

*Primary Examiner* — Christine H Matthews
(74) *Attorney, Agent, or Firm* — Hawaii Patent Services; Nathaniel K. Fedde; Kenton N. Fedde

(57) ABSTRACT

The concentration of substance in blood is measured non-invasively, with high accuracy and with simple configuration. Laser light generated by a light source is locally irradiated on the body epithelium of a subject, and the resulting diffused reflected light is detected by a light detector. The laser light has a wavelength of 9.26 μm. The laser light is generated by converting and amplifying pulsed excitation light from an excitation light source to a long wavelength. A plate-shaped window that is transparent to mid-infrared light is brought in close contact with the body
(Continued)

epithelium. The glucose concentration in interstitial fluid can be calculated using normalized light intensity calculated from a signal ratio of signals from a monitoring light detector and light detector.

13 Claims, 14 Drawing Sheets

(51) Int. Cl.
| | |
|---|---|
| *A61B 5/145* | (2006.01) |
| *G02F 1/35* | (2006.01) |
| *G02F 1/39* | (2006.01) |
| *A61B 90/30* | (2016.01) |
| *A61B 90/00* | (2016.01) |
| *H01S 3/16* | (2006.01) |
| *H01S 3/223* | (2006.01) |

(52) U.S. Cl.
CPC ........... *G01N 21/55* (2013.01); *G02F 1/3501* (2013.01); *G02F 1/39* (2013.01); *A61B 2090/306* (2016.02); *A61B 2090/3614* (2016.02); *A61B 2562/0233* (2013.01); *G02F 2001/3507* (2013.01); *H01S 3/1603* (2013.01); *H01S 3/1643* (2013.01); *H01S 3/2232* (2013.01)

(56) References Cited

U.S. PATENT DOCUMENTS

| | | | |
|---|---|---|---|
| 5,370,114 | A | 12/1994 | Wong et al. |
| 5,666,956 | A | 9/1997 | Buchert |
| 9,041,923 | B2 | 5/2015 | Messerchmidt |
| 2004/0024541 | A1 | 2/2004 | Uchida et al. |
| 2006/0173353 | A1 | 8/2006 | Uchida |
| 2006/0281982 | A1 | 12/2006 | Grata et al. |
| 2007/0093702 | A1* | 4/2007 | Yu ................... A61B 5/14552 600/326 |
| 2007/0123759 | A1 | 5/2007 | Grata et al. |
| 2007/0213607 | A1* | 9/2007 | Mandelis ................ A61B 5/01 600/316 |
| 2008/0068592 | A1 | 3/2008 | Uchida |
| 2009/0105564 | A1 | 4/2009 | Tokita |
| 2009/0128805 | A1 | 5/2009 | Tokita |
| 2010/0298673 | A1 | 11/2010 | Herrmann |
| 2012/0088486 | A1 | 4/2012 | Messerchmidt |
| 2012/0238844 | A1 | 9/2012 | Grata et al. |
| 2014/0131578 | A1 | 5/2014 | Hruska et al. |
| 2015/0260572 | A1 | 9/2015 | Malcolm et al. |

FOREIGN PATENT DOCUMENTS

| | | |
|---|---|---|
| CN | 101557752 A | 10/2009 |
| JP | 54-83474 A | 7/1979 |
| JP | 11178799 A | 7/1999 |
| JP | 2001-503999 A | 3/2001 |
| JP | 2005-080710 A | 3/2005 |
| JP | 2005348912 A | 12/2005 |
| JP | 2008-046246 A | 2/2008 |
| JP | 2012-191969 A | 10/2012 |
| WO | WO2006051778 | 5/2006 |
| WO | 2006079797 A2 | 8/2006 |
| WO | 2006132218 A1 | 12/2006 |
| WO | WO2007141859 | 10/2007 |
| WO | WO2014033465 | 3/2014 |

OTHER PUBLICATIONS

Japan Patent Office. Office action of foreign counterpart, dated Sep. 10, 2019.
The State Intellectual Property Office of the People'S Republic of China. Office action of foreign counterpart, dated Nov. 26, 2019.
European Patent Office. Supplementary Partial European Search Report for EP 16 74 0127. 17 pages, dated Apr. 20, 2018. Munich, Germany.
Takeo Uemura, Kenro Nishida, Michiharu Sakakida, Kenshi Ichinose, Seiya Shimoda and Motoaki Shichiri, [Non-invasive blood glucose measurement by Fouier transform infrared spectroscopic analysis through the mucous membrane of the lip:application of a chalcogenide optical fiber system], Frontiers of Medical and Biological Engineering, vol. 9, No. 2, p. 137(1999).
Miguel A.Pleitez, Tobias Lieblein, Alexander Bauer, Otto Hertzberg, Hermann Von Lilienfeld-Toal, and Werner Mantele, [In-Vivo Non-invasive Monitoring of Glucose Concentration in Human Epidermis by Mid-Infrared Pulsed Photoacoustic Spectroscopy], Analytical Chemistry, vol. 85, p. 1013(2013).
Meinke et al. "Two-wavelength carbon dioxide laser application for in-vitro blood glucose measurements". Journal of Biomedical Optics vol. 13, No. 1. pp. 014021-1 to 014021-6. Jan. 2008.
Yu et al. "In vitro glucose measurement using tunable mid-infrared laser spectroscopy combined with fiber-optic sensor" Biomedical optics express vol. 5, No. 1. pp. 275-86. Dec. 17, 2013.
Vodopyanov et al. "Grating tunable 4-14 μm GaAs optical parametric oscillator pumped at 3 μm," ., Optics Express, vol. 22, No. 4, Feb. 14, 2014. pp. 4131-4136. Feb. 14, 2014.
Extended European search report, dated Aug. 8, 2018. 17 Pages.
Japan Patent Office. Office action of foreign counterpart Japan Patent Application 2018-187388, dated Mar. 17, 2020.
European Patent Office. Office action of foreign counterpart European Patent Application 16740127.2-1209, dated May 11, 2020.

\* cited by examiner

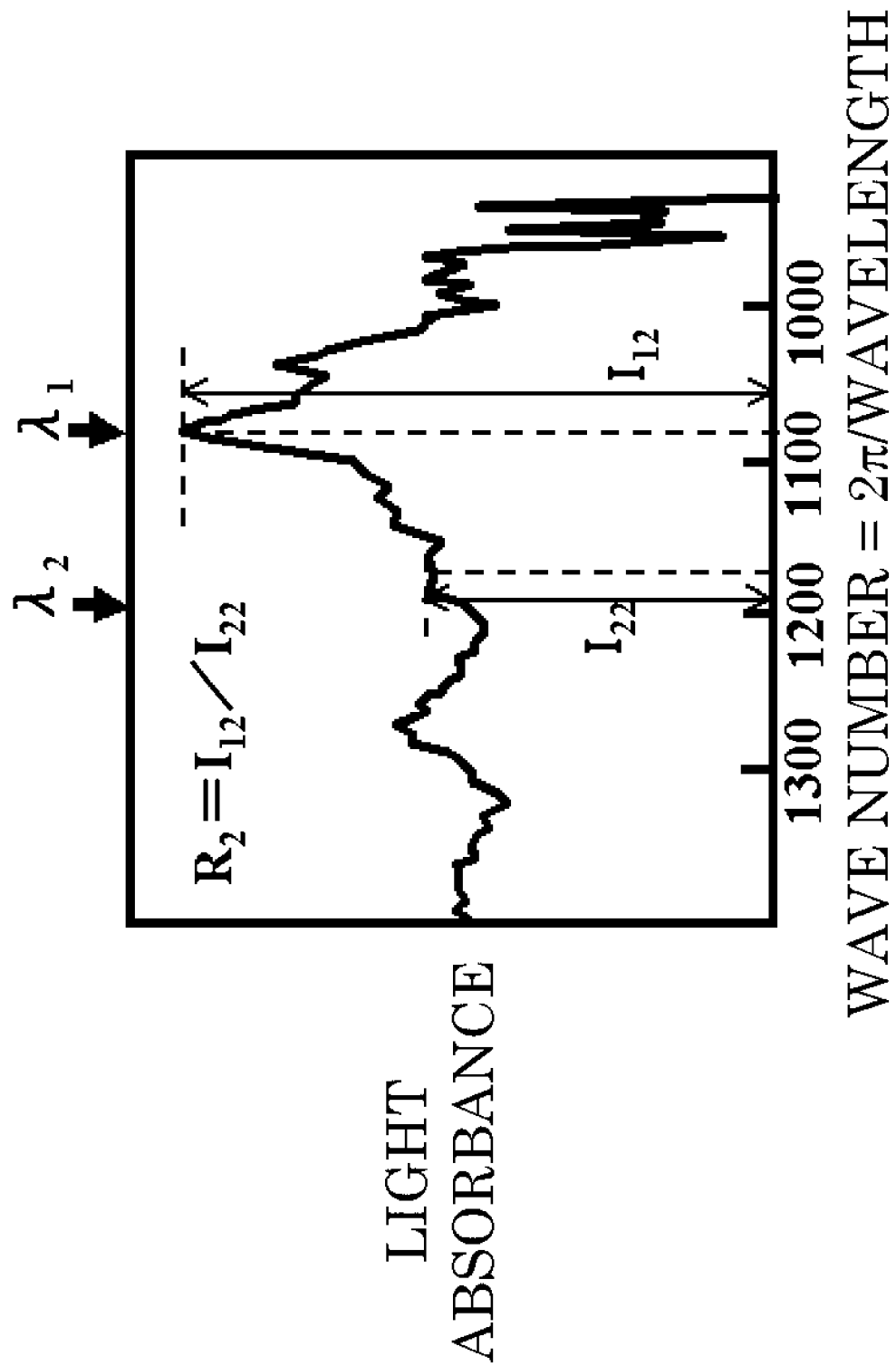

DEVICE FOR MEASURING CONCENTRATION OF SUBSTANCE IN BLOOD, AND METHOD FOR MEASURING CONCENTRATION OF SUBSTANCE IN BLOOD

TECHNICAL FIELD

The present invention relates to a device for measuring the concentration of a substance in blood and measures a substance (glucose, lipids, and the like) in blood non-invasively, and relates to a method for measuring the concentration of a substance in blood.

BACKGROUND ART

In recent years, the amount of people having lifestyle-related diseases resulting from obesity due to a lack of exercise, accumulation of stress and the like is increasing, and these lifestyle-related diseases are caused by metabolic syndrome in which blood glucose, blood lipids and blood pressure rise. Therefore, for the prevention and treatment of lifestyle-related diseases, investigating the state of the blood glucose level, blood lipid level, and blood pressure on a daily basis is extremely important. Of these, daily management of the blood glucose level is required in order to prevent serious complications in patients with diabetes, which is one of the lifestyle-related diseases. The blood glucose level referred to here is more precisely the concentration of glucose that is included in the blood. In order to measure the blood glucose level, there are invasive methods in which a blood sample is taken from a patient and chemical analysis of the blood is performed, and there are non-invasive methods in which analysis of blood in the body is performed without taking a blood sample.

In invasive methods, it is possible to apply various chemical analysis methods on the collected blood, so it is possible to measure the blood glucose level with sufficient accuracy. In order to manage the blood glucose level on a daily basis, it is necessary to measure the change over time of the blood glucose level by performing measurement several times a day using a self blood-glucose meter (performing self-monitoring of the blood glucose level). When doing so, it is necessary to puncture a finger or the like and collect blood, and in addition to being bothersome for the patient, causes psychological stress and suffering, as well as causes various problems such as the risk of infection and the like. Furthermore, the cost of expendable items such as puncture needles and sensor chips pose a large burden, and since it costs more than 200,000 yen per year, for example, the economic burden on the patient becomes large.

Therefore, from the aspect of eliminating psychological and physical distress of a patient, and preventing infection, a micro-invasive type blood glucose meter capable of continuously measuring the blood glucose level by a method of applying a patch with a needle-type sensor attached to the back side (Continuous Glucose Monitoring (CGM): continuous type subcutaneous blood glucose measurement system) is being sold in the USA and in Japan. In Japan, such a patch type sensor was approved in the fall of 2009 as a medical device by the Ministry of Health, Labor and Welfare, and in February 2010, this patch type sensor became applicable to insurance. However, this patch type sensor is still invasive in that the needle-type sensor is kept in a state of being stuck under the skin and burdens the patient with annoyance and stress. In this method, the glucose concentration in the interstitial fluid (epithelial interstitial fluid) right under the epidermis is measured. For example, when the blood glucose level changes over time, there is a time difference in the change over time of the glucose concentration and blood glucose level in the interstitial fluid, however, since there is a strong relationship between them, it is actually possible to recognize the glucose concentration in the interstitial fluid as the blood glucose level.

On the other hand, in non-invasive methods, such problems do not occur because stress to the patient is small, and these methods are preferably used for daily management of the blood glucose level. However, non-invasive methods, when compared with invasive methods in which the glucose concentration in the blood is measured directly, are limited as methods for detecting glucose, so at present the measurement accuracy is inferior in comparison with invasive methods. Therefore, attempts are being made to develop a non-invasive blood glucose level measuring method that is capable of measuring the blood glucose level with the same accuracy as invasive methods.

Of non-invasive methods, optical methods are widely used. In this kind of measuring method, as described in Patent Document 1, Patent Document 2 and the like for example, the blood glucose concentration is measured by absorption in blood of light that is transmitted though the skin. Here, laser light is used, and the laser light is locally irradiated onto the body using optical fiber or the like, and the absorption of the light by glucose in the blood is measured by measuring the intensity of transmitted light or scattered light from the body. The laser light that is used here must be such that, in addition to being able to measure the absorption by glucose, the light must be able to reach inside the body, and as this laser light, light in the near infrared region (wavelength of about 1 to 2 μm) of which there is little absorption by the skin and the like is widely used. Near-infrared light is such that little of the light is absorbed by hemoglobin and water, so the light easily reaches the inside of the body, and the change in the intensity of the laser light due to absorption near the wavelength of 1.5 μm in the glucose absorption spectrum is measured. Therefore, it is possible to measure the glucose concentration in the blood by detecting the intensity of light after being transmitted through blood in the body, and comparing that intensity with the intensity of the incident light.

In the technology in Patent Document 1, near infrared light is irradiated onto the subcutaneous tissue (dermal tissue) under a nail via optical fiber for irradiation, then diffused reflected light from the subcutaneous tissue is guided to light receiving means by optical fiber for receiving light and measurement of the absorption spectrum is performed. The blood glucose level is calculated from the measurement results (the blood glucose level is estimated by measuring the glucose concentration in the dermal tissue as a substitute property of the blood glucose level). When doing this, the blood glucose level is calculated by using a database of a large number of measurement data, variables related to bodies, and measurement results by an invasive method, and substituting in measurement values of the spectrum into a calibration formula that is obtained by multivariate analysis. This is similar to blood glucose measurement that uses a correlation between the interstitial fluid (ISF) and the blood glucose level that is used by a micro-invasive blood glucose meter glucose watch (manufactured by Cygnus USA) that uses reverse iontophoresis that is currently in practical use in the USA.

In this way, when measuring the blood glucose level using near infrared light, multivariate analysis is necessary even when monochromatic light is used. The general reason for this is that when using near infrared light, the absorption signal, in order to handle harmonics of glucose (harmonic sound and coupled sound of the reference oscillation in the mid-infrared region), is very weak when compared with infrared light, and the attribution of the band is not clear. Therefore, in order to perform quantitative analysis and qualitative analysis of glucose using near infrared spectroscopic analysis, statistical processing such as multivariate analysis is necessary.

Moreover, being able to measure the blood glucose level by non-invasive methods by recognizing the absorption peak by glucose from an FTIR absorption spectrum after transmembrane penetration of blackbody radiated light with a wide spectrum in the mid-infrared region from a nichrome wire heater, without using monochromatic light such as described above is described in Non-patent document 1. Furthermore, a method for measuring blood glucose using blackbody radiated light in the mid-infrared region from body heat is proposed in Patent Document 3.

Moreover, as described in Patent Document 4, it is also possible to measure the glucose concentration in the interstitial fluid (epithelial interstitial fluid) just below the epidermis instead of blood deep inside the body. In the technology described in Patent Document 3, technology is described in which the glucose concentration in this epithelial interstitial fluid is calculated from the infrared light absorption spectrum using plural laser light sources. Furthermore, technology is described in Non-patent Document 2 in which the glucose concentration is estimated by performing mulitvariate analysis by performing a wavelength sweep of a specific wavelength region using a quantum cascade laser in the mid-infrared region, and measuring the change in the photoacoustic signal that is due to a change in the glucose concentration in the epithelial interstitial fluid.

PRIOR ART LITERATURE

Patent Literature

Patent Document 1: JP2005080710 (A)
Patent Document 2: JP2012191969 (A)
Patent Document 3: JP2001503999 (A)
Patent Document 4: US Patent Application Publication No. US2007/0213607

Non-Patent Literature

Non-patent Document 1: "Non-invasive blood glucose measurement by Fourier transform infrared spectroscopic analysis though the mucous membrane of the lip: application of a chalcogenide optical fiber system", Takeo Uemura, Kenro Nishida, Michiharu Sakakida, Kenshi Ichinose, Seiya Shimoda, and Motoaki Shichiri; Frontiers of Medical and Biological Engineering, Vol. 9, No. 2, p137 (1999) Non-patent Document 2: "In-Vivo Noninvasive Monitoring of Glucose Concentration in Human Epidermis by Mid-Infrared Pulsed Photoacoustic Spectroscopy", Miquel A. Pleitez, Tobia Lieblein, Alex ander Bauer, Otto Hertzberg, Hermann von Lilienfeld-Toal, and Werner Mantele; Analytical Chemistry, Vol. 85, p1013 (2013)

SUMMARY OF THE INVENTION

Problems to be Solved by the Invention

Although the near infrared light that is used in Patent Documents 1 and 2 easily reaches to the capillaries of the epithelium of the body, the rate of change in the light intensity due to absorption by glucose of near-infrared light (for example, at a wavelength of 1.5 μm) is only about 0.4%. Therefore, the light intensity that is detected it greatly affected by various substances (proteins, lipids and the like) in the blood other than glucose. Moreover, absorption that is due to such substances other than glucose is greatly affected by environmental conditions (body temperature and the like), so the uncertainty of the absorption increases. Consequently, the measurement error of the glucose concentration is as large as about 20 to 30 mg/dL, and that is very inferior when compared with that in the case of invasive methods.

However, in Non-patent Documents 1 and 2 and Patent Documents 3 and 4, infrared light having a wavelength longer than these is used, so the effect on absorption due to glucose can be made to be sufficiently larger than the effect on absorption due to biological components other than glucose. However, in this case, the transmittance of light in the body is low, so the intensity of light that is detected is low. Furthermore, the peak power (peak power) per single wavelength that is obtained from the light source that is used in this wavelength range is typically very low when compared with the case of near-infrared light, and the intensity of background light in this wavelength range is high, so it is difficult to obtain sufficient S/N that is necessary for measuring the blood glucose level. Alternatively, it is necessary to use a measurement device having a complicated configuration that uses plural laser light sources such as in the technology described in Patent Document 4, and furthermore, as in the technology described in Non-patent Document 2, a complex analysis method such as multivariate analysis or the like that measures the change in a photoacoustic signal due to change in the glucose concentration in the epithelial interstitial fluid becomes necessary, or the measurement device or analysis device becomes large and complicated, and, for example, is not suited to measuring the change over time of the blood glucose level.

In other words, it is difficult to measure substance in the blood non-invasively and with high accuracy using a simple configuration.

Taking the problems described above into consideration, an object of the present invention is to provide an invention that solves the problems above.

Means for Solving Problems

In order to solve the problems above, the present invention is configured as described below.

The device for measuring the concentration of substance in blood of the present invention is a device for measuring the concentration of substance in blood that measures the concentration of substance that is included in the blood of a body, that includes: a laser oscillator that oscillates a first laser light having a wavelength that is within the range 2.5 μm to 12 μm, and that is absorbed by the substance; a light-guiding unit that guides the first laser light to the body, and guides first diffused reflected light that is generated by the first laser light from the body; and a light-detection unit that detects the light intensity of the first diffused reflected light.

In the device for measuring the concentration of substance in blood, the light-guiding unit includes: an incident-side optical waveguide that guides the first laser light to the body; and an exit-side optical waveguide that guides the first diffused reflected light to the light-detection unit.

In the device for measuring the concentration of substance in blood, the light-guiding unit guides the first laser light to the body at an incident angle of 35° to 85°.

In the device for measuring the concentration of substance in blood, the laser oscillator is an optical parametric oscillator that uses excitation light having a wavelength that is different than the first laser light and that is emitted from an excitation light source, and that oscillates the first laser light by first non-linear optical crystal.

In the device for measuring the concentration of substance in blood, the excitation-light source is a passive Q-switched Nd:YAG laser or passive Q-switched Yb:YAG laser.

In the device for measuring the concentration of substance in blood, the excitation-light source oscillates a pulsed excitation light with a repetition frequency of 1 Hz or greater.

In the device for measuring the concentration of substance in blood, the laser oscillator is a carbon dioxide gas laser oscillator.

In the device for measuring the concentration of substance in blood, the laser oscillator oscillates a second laser light having a wavelength that is within the range 2.5 to 12 μm and that is different than that of the first laser light, and that has a characteristic of being absorbed by the substance less than the first laser light; and in the light-guiding unit the incident-side optical waveguide guides the second laser light to the body, and the exit-side optical waveguide guides second diffused reflected light that is generated by the second laser light to the light-detection unit.

In the device for measuring the concentration of substance in blood, the optical parametric oscillator includes a second non-linear optical crystal that generates the second laser light using the excitation light.

In the device for measuring the concentration of substance in blood, in the optical parametric oscillator, the first non-linear optical crystal and the second non-linear optical crystal are arranged in series on the optical path.

In the device for measuring the concentration of substance in blood, the laser oscillator oscillates a second laser light having a wavelength within the range 2.5 to 12 μm and that is different than that of the first laser light, and that has a characteristic of being absorbed by the substance less than the first laser light; and in the light-guiding unit, the incident-side optical waveguide guides the second laser light to the body, and the exit-side optical waveguide guides second diffused reflected light that is generated by the second laser light to the light-detection unit.

In the device for measuring the concentration of substance in blood, the laser oscillator oscillates the first laser light and the second laser light in a pulsed shape with a repetition frequency of 1 Hz or greater.

The device for measuring the concentration of substance in blood of the present invention further includes a window that is inserted between the light-guiding unit and the body, that is made using a material that allows the second laser light to pass through, and that has a shape so that when inserted between the light-guiding unit and the body and brought in contact with the body, a space is formed between the window and the body through which the first laser light and the second laser light pass.

In the device for measuring the concentration of substance in blood, the substance is glucose; and the wavelength of the first laser light is within the range 7.0 μm to 11 μm.

The method for measuring the concentration of substance in blood of the present invention is a method for measuring the concentration of substance in blood that measures the concentration of substance included in blood of a body, and measures the concentration of substance in epithelial interstitial fluid of the body by light intensity of first diffused reflected light that is generated by irradiating the body with a first laser light having a wavelength within the range 2.5 μm to 12 μm and that is absorbed by the substance.

The method for measuring the concentration of substance in blood that guides the first laser light to the body at an incident angle of 35° to 85°.

The method for measuring the concentration of substance in blood that oscillates the first laser light by optical parametric oscillation.

The method for measuring the concentration of substance in blood that oscillates the first laser light by a carbon dioxide gas laser oscillator.

The method for measuring the concentration of substance in blood that measures the concentration of the substance in epithelial interstitial fluid of the body by the light intensity of the first diffused reflected light and the light intensity of second diffused reflected light that is generated by the second laser light.

In the method for measuring the concentration of substance in blood, the optical path of the first laser light and the optical path of the second laser light overlap, and the optical path of the first diffused reflected light that is incident on a light-detection unit that detects the light intensity, and the optical path of the second diffused reflected light that is incident on the light-detection unit overlap.

In the method for measuring the concentration of substance in blood, the substance is glucose, and the wavelength of the first laser light is within the range 7.0 μm to 11 μm.

Effect of Invention

The present invention is configured as described above, so it is possible to measure the concentration of substance in blood non-invasively, with high accuracy and with simple configuration.

BRIEF DESCRIPTION OF THE DRAWINGS

FIG. 9A to FIG. 9C schematically illustrate the relationship between the absorption and wave number (absorption spectrum) for three kinds of glucose concentration.

EMBODIMENTS FOR CARRYING OUT THE INVENTION

Figure 1:
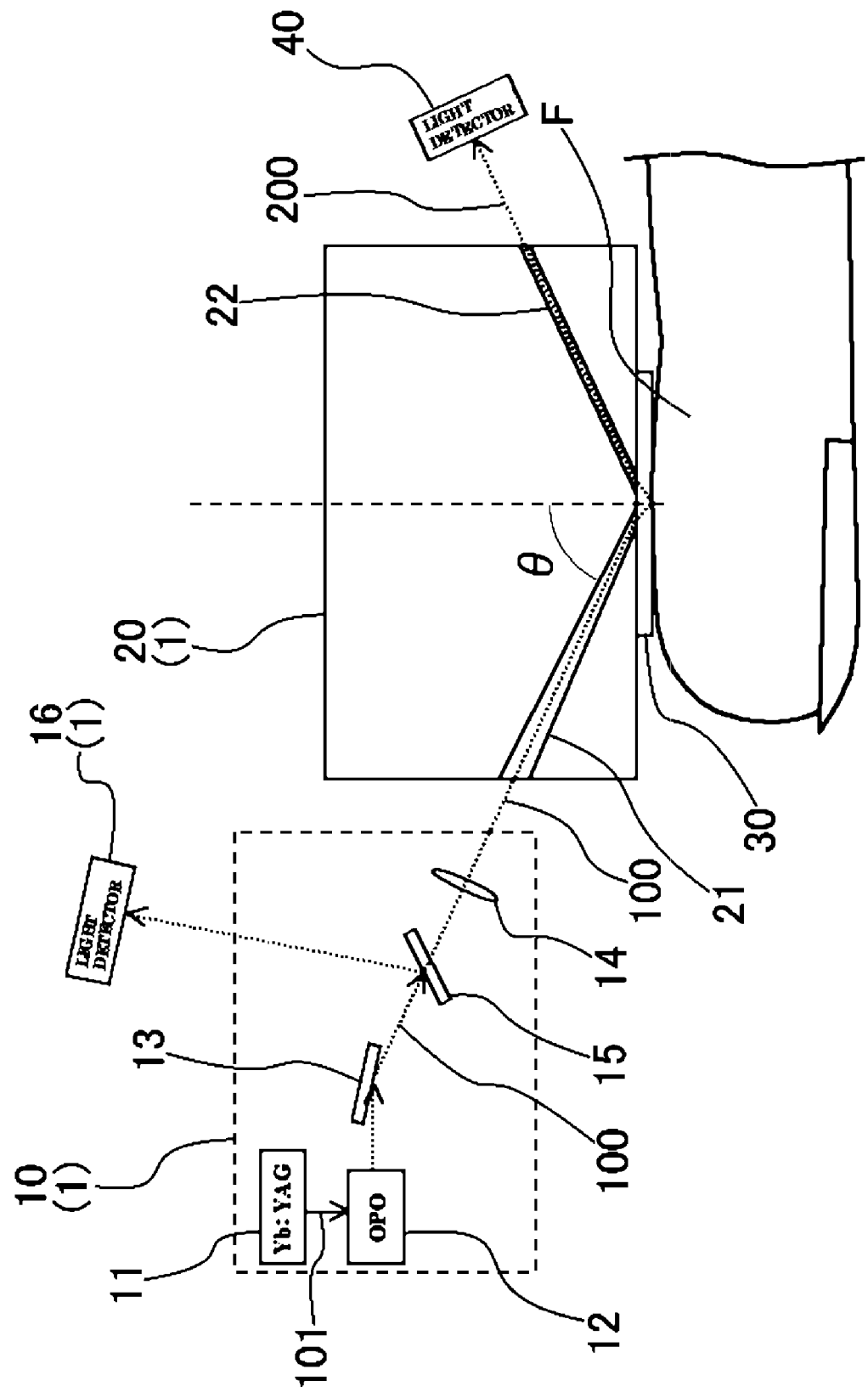
FIG. 1 is a drawing (1 of 2) that illustrates the configuration of a blood glucose meter of an embodiment of the present invention.

In the following, a blood glucose meter (device for measuring the concentration of a substance in the blood), or a method for measuring the blood glucose level (method for measuring the concentration of a substance in the blood) of an embodiment of the present invention will be explained. FIG. 1 illustrates the configuration of this blood glucose meter 1. This blood glucose meter 1 is a non-invasive type, and locally irradiates laser light (first laser light) 100 that is generated by a light source 10 onto the epithelium of the body (body) F of a test subject, and the diffused reflected light (first diffused reflected light) 200 thereof is detected by a light detector (light detection unit) 40. Here, the substance that is included in the blood that is the object to be measured is glucose. More correctly, as described in Patent Document 3, it is not the blood, but rather the glucose concentration in the epithelial interstitial fluid that is measured, and this can be recognized as the blood glucose level. In this case, it is necessary to measure the glucose concentration in the interstitial fluid directly below the skin, and in this case it is particularly preferable that mid-infrared light that does not penetrate deep inside the body because of its large absorption be used. Furthermore, in the case of light in the near-infrared region, overlapping of harmonics and coupled sound of reference vibration has an effect on measurement, however, in the case of light in the mid-infrared range, such effects are small, so the measurement of the hydroxyl group of glucose can be performed more accurately than in the case of near-infrared light. In the blood glucose meter and the blood glucose level measurement method, mid-infrared light is used and what is actually measured is the glucose concentration in the interstitial fluid.

As illustrated in FIG. 1, the laser light 100 that is used here is mid-infrared light, the wavelength, for example, is 9.26 μm, and the light is oscillated by a light source 10. In the light source 10, laser light 100 is generated by converting an excitation light 101 having a wavelength that is shorter than the pulse-like mid-infrared light that is oscillated from an excitation light source 11 to a long wavelength while at the same time amplifying the light by an OPO (optical parametric oscillator) 12. This optical parametric oscillation is described, for example, in JP2010281891 (A). Here, the wavelength oscillated by optical parametric oscillation is taken to be 9.26 μm. This wavelength is set as a wavelength with large absorption by glucose. This wavelength, for example, can be set according to a spectrum of a fluid that includes glucose as described in Non-patent Document 1 above.

As the excitation light source 11, it is particularly preferred that a Q-switched Nd:YAG laser (oscillation wavelength of 1.064 μm) or a Q-switched Yb:YAG laser (oscillation wavelength of 1.030 μm) capable of generating a pulse-like excitation light 101 having a wavelength that is shorter than mid-infrared light be used. A passive Q-switched Nd:YAG laser or Yb:YAG laser that is capable of automatically performing a switching operation using a supersaturated absorber is able to simplify and miniaturize the excitation light source 11 and the configuration for controlling the excitation light source 11, so is particularly preferred. In Q-switched oscillation, it is possible, for example, to oscillate an excitation light 101 with a repetition of 10 Hz or greater and pulse width of about 8 ns.

Figure 2:
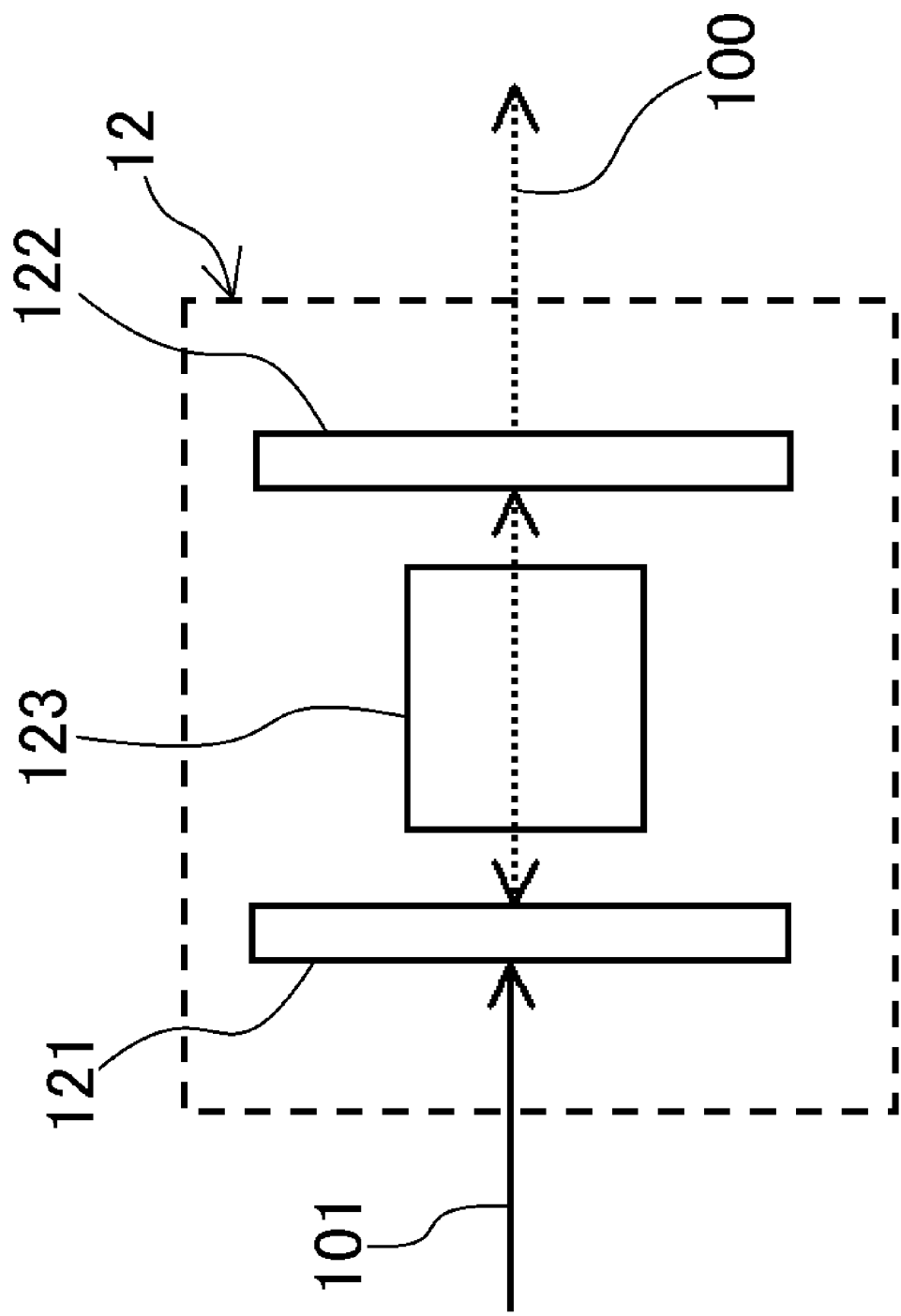
FIG. 2 illustrates the configuration of an optical parametric oscillator that is used in a blood glucose meter of an embodiment of the present invention.

FIG. 2 schematically illustrates the configuration of the OPO 12. In the OPO 12, a non-linear optical crystal 123 is placed between an incident side half mirror 121 and an exit side half mirror 122. The excitation light 101 that passes through the incident side half mirror 121 enters on the non-linear optical crystal 123, and is converted to light having a wavelength of 9.26 μm that is the wavelength set by the non-linear optical crystal 123, and when the light is reflected and confined between the incident side half mirror 121 and exit side half mirror 122, the light is amplified by optically parametric amplification. The amplified light passes through the exit side half mirror 122, becomes laser light 100 and is outputted. In FIG. 1, for convenience, the direction of the laser light 100 that is emitted from the OPO 12 and the direction of the excitation light 101 are illustrated as being different, however, the directions are appropriately adjusted using a suitable reflector. As the non-linear optical crystal 123, AgGaS that is suitable for this kind of wavelength conversion is used under the condition of phase matching. By adjusting the type and matching conditions of the non-linear optical crystal 123, it is possible to adjust the wavelength of the emitted laser light 100. As the non-linear optical crystal, it is also possible to use GaSe, $ZnGeP_2$, $CdSiP_2$, $LiInS_2$, $LiGaSe_2$, $LiInSe_2$, $LiGaTe_2$ and the like. The laser light 100 that is emitted from the OPO 12 has a repetition frequency and a pulse width (for example, about 8 ns) that corresponds to the excitation light 101, and with this short pulse width, the peak output has a high intensity of 10 W to 1 kW.

The laser light 100 is collected by the condenser lens 14 after the path is adjusted by the mirror 13, then enters into the incident side optical waveguide 21 that is provided in a light-guiding unit 20. However, a beam splitter 15 that is configured with a half mirror provided between the mirror 13 and condenser lens 14, and part of the laser light 100 is branched off to be used for a monitor. The part of the laser light 100 that is branched off is detected by a monitoring light detector (monitoring light detector unit) 16, so even when there is fluctuation in the intensity of the laser light 100 itself, that fluctuation can be recognized from the output of the monitoring light detector 16.

A mostly flat plate shaped window 30 that is made using a material that is transparent to mid-infrared light is provided between the light-guiding unit 20 and the body epithelium F, and the window 30 and body epithelium F come in close contact. Laser light 100 that passes through the window 30 is incident on the body epithelium F. The angle of incidence of the laser light 100 with respect to the body epithelium F is determined by the angle of the incident side optical waveguide 21 with respect to the bottom surface of the light-guiding unit 20 (top surface of the window 30) and the refraction angle of the laser light 100 that is incident on the window 30 at this angle.

The laser light 100 is incident on the body epithelium F and passes through the epithelial stromal tissue of the body, and the scattered or diffused reflected light 200 passes though the window 30 again, then passes through the exit side optical waveguide 22 that is formed in the light-guiding unit 20 and is obtained on the outside of the light-guiding unit 20. The direction from which the diffused reflected light 200 is obtained is set by the angle of the exit-side optical waveguide 22 with respect to the bottom surface of the light-guiding unit 20 (top surface of the window 30), and this angle is the same as that of the incident-side optical waveguide 21 described above. This diffused reflected light 200 is detected by a light detector 40 that detects mid-infrared light and outputs that light as an electrical signal.

The light-guiding unit 20 is made using a metal material such as stainless steel or the like, and inside the light-guiding unit 20, an incident side optical waveguide 21 and an exit side optical waveguide 22 are formed as through holes. The inside surfaces of the incident side optical waveguide 21 and exit side optical waveguide 22 are coated in order to increase the light reflectance. It is possible to use a multilayer dielectric film as the coating material for increasing the light reflectance. Moreover, the incident side optical waveguide 21 is formed such that the exit side thereof gradually becomes narrower than the incident side. As a result, it is possible to collect light by the incident side optical waveguide 21 as well, and it is possible to limit the irradiation range of the irradiated laser light 100.

Figure 3:
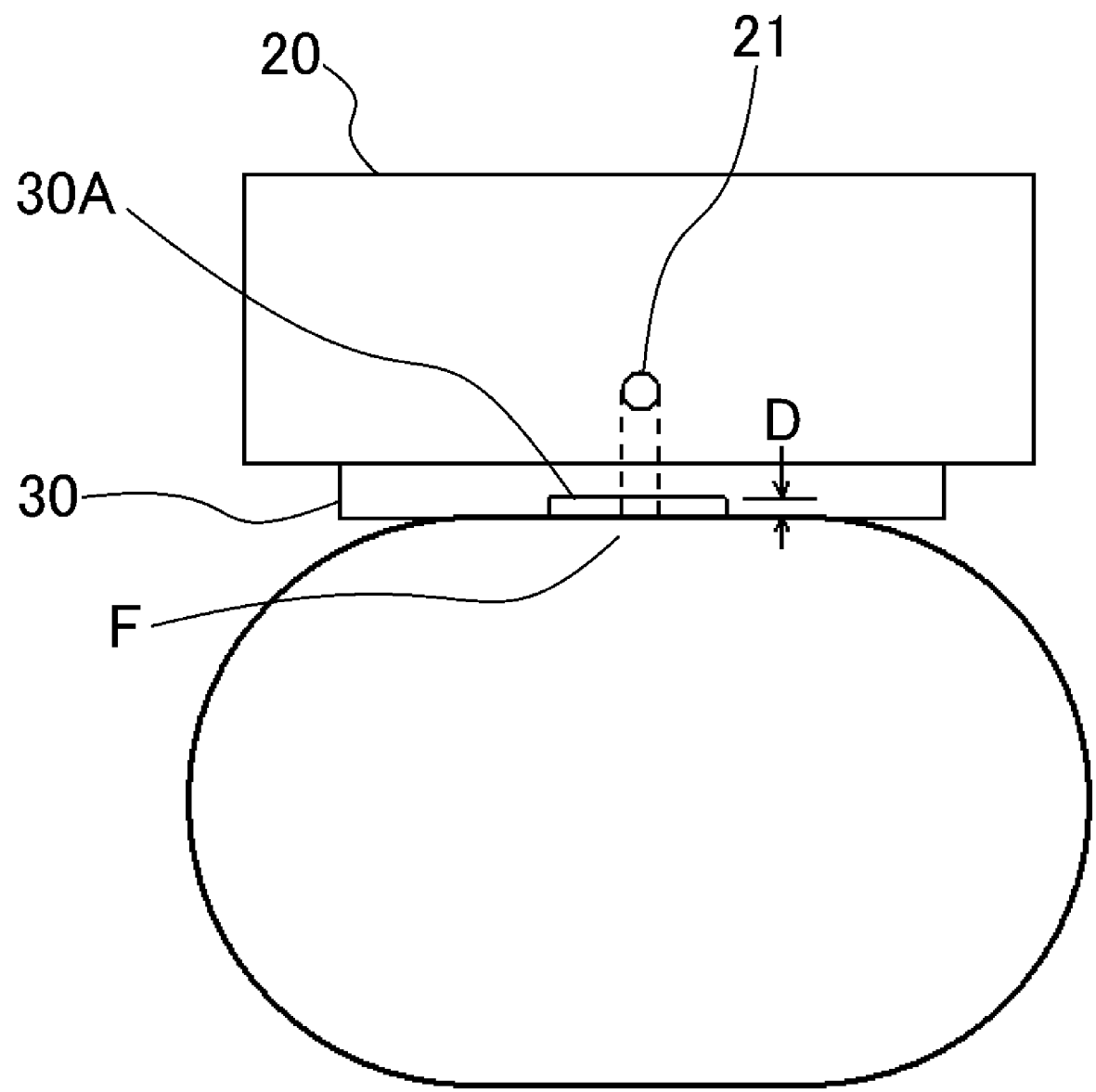
FIG. 3 is a drawing (2 of 2) that illustrates the configuration of a blood glucose meter of an embodiment of the present invention.

The window 30 is made using a material such as ZnSe or the like that is transparent to mid-infrared light, and the surface of the window 30 is coated with a non-reflective coating. FIG. 3 illustrates the positional relationship of the light-guiding unit 20, the window 30 and the body epithelium F as seen from the left side (incident side) in FIG. 1. For example, the refractive index of ZnSe with respect to mid-infrared light is about 2.4, and the refraction angle of the laser light 100 in the window 30 is determined by the refractive index. As will be described later, when measuring the glucose concentration in the epithelial interstitial fluid in particular, there is an optimum range for the incident angle of the laser light 100 with respect to the body epithelium F.

Moreover, a slit 30A that is a concave section is provided on the bottom surface side in FIG. 3 of the window 30 so that when the window 30 is brought into close contact with a finger, a gap having a width D is formed between the window 30 and the body epithelium F at the areas around the outlet of the incident side optical waveguide 21 and the inlet of the exit side optical waveguide 22 of the light-guiding unit 20. As a result, direct contact between the body epithelium F and the window 30 is suppressed at the portions where the laser light 100 enters and the diffused reflected light 200 exits regardless of a condition of close contact between the window 30 and the finger, and an air layer (void) is always formed between the window 30 and the finger. The refractive index of the ZnSe of the window 30 is large, so at the interface between the window 30 and the body epithelium F, it is easy for the laser light 100 to be totally reflected, and particularly, the state of this total reflection is greatly influenced by the condition of close contact between the window 30 and the body epithelium F, however, by stabilizing this state with the slit 30A and by providing this kind of space between the window 30 and the body epithelium F, it is possible to stably maintain a state in which total reflection is suppressed. The thickness of the window 30 is set, for example, to be 500 µm, the width of the slit 3A is 700 µm, and the space D is about 400 µm. However, the body epithelium F is soft so there is close contact between the body epithelium F and the window 30 at locations other than where the slit 30A is provided. In FIG. 3, it is possible for configuration to be such that a slit 30A is not provided and the bottom surface side of the window 30 is a flat shape, and to essentially form a slit 30A by applying tape or the like to the outer sides of the portion that corresponds to the slit 30A to form convex shapes on the bottom side of this portion.

As the light detector 40 and monitoring light detector 16, an HgCdTe infrared detector that is cooled with liquid nitrogen is used for example. In this case, the light detector 40 detects diffused reflected light 200 having an intensity that is high enough that background light can be ignored. When doing this, by cooling with liquid nitrogen to about 77K, it is possible to detect the light intensity of diffused reflected light 200 with a high S/N ratio. Moreover, even when presuming that the intensity of the laser light 100 that is incident on the body epithelium F fluctuates, accurate analysis as will be described later becomes possible by using the output (detected intensity) of the light detector 40 that is normalized by the output (detected intensity) of the monitoring light detector 16.

In a typical blood glucose meter that uses light, near-infrared light having transmittance into the body is mainly used as monochromatic light used for analysis. In the configuration described above, mid-infrared light (laser light 100) having low transmittance into the body is used as the light used for analysis. Therefore, only the epidermis portion is observed, and observation is not easily affected by other biological components that are present in deeper portions. Moreover, as described above, there is little adverse effect on measurement due to overlapping of harmonics and coupled sound of reference vibration. On the other hand, by using an excitation light source 11 and OPO 12, it is possible to increase the intensity of the laser light 100 that enters into the body epithelium F, it is possible to obtain a laser light 100 having a high intensity that is about $10^3$ to $10^5$ times higher when compared with a typical light source of infrared light having a wavelength of 9.26 µm (for example, a quantum cascade laser). Therefore, the intensity of the diffused reflected light 200 that is detected by the light detector 40 can be made to be sufficiently higher than the background light, and when compared with typical technology that uses infrared light in the same wavelength range (Patent Documents 3 and 4, Non-patent documents 1 and 2 and the like), it is possible to perform measurement with much higher accuracy. Here, the laser light 100 and the diffused reflected light 200 are monochromatic and have high intensity, so it is possible to calculate the glucose concentration in the interstitial fluid by using the normalized light intensity that is calculated from the signal ratio of the monitoring light detector 16 and light detector 40, it is possible to make a 1-to-1 correlation with this and the glucose concentration in blood, and it is not necessary to perform spectrum analysis, multivariate analysis or the like. Furthermore, there is no need to take time for a wavelength sweep as in the photoacoustic optical method that uses a quantum cascade laser, so measurement can be performed in a short period of time.

Therefore, what is required for the light detector 40 or the monitoring light detector 16 is only detection of the light intensity. Consequently, the S/N ratio of the output decreases a little, however, liquid nitrogen that can cool to 77K is not used and it is possible to use electron cooling or the like that is a cooling method in which the temperature is higher but can be used more easily than in the case of using liquid nitrogen.

Figure 4:
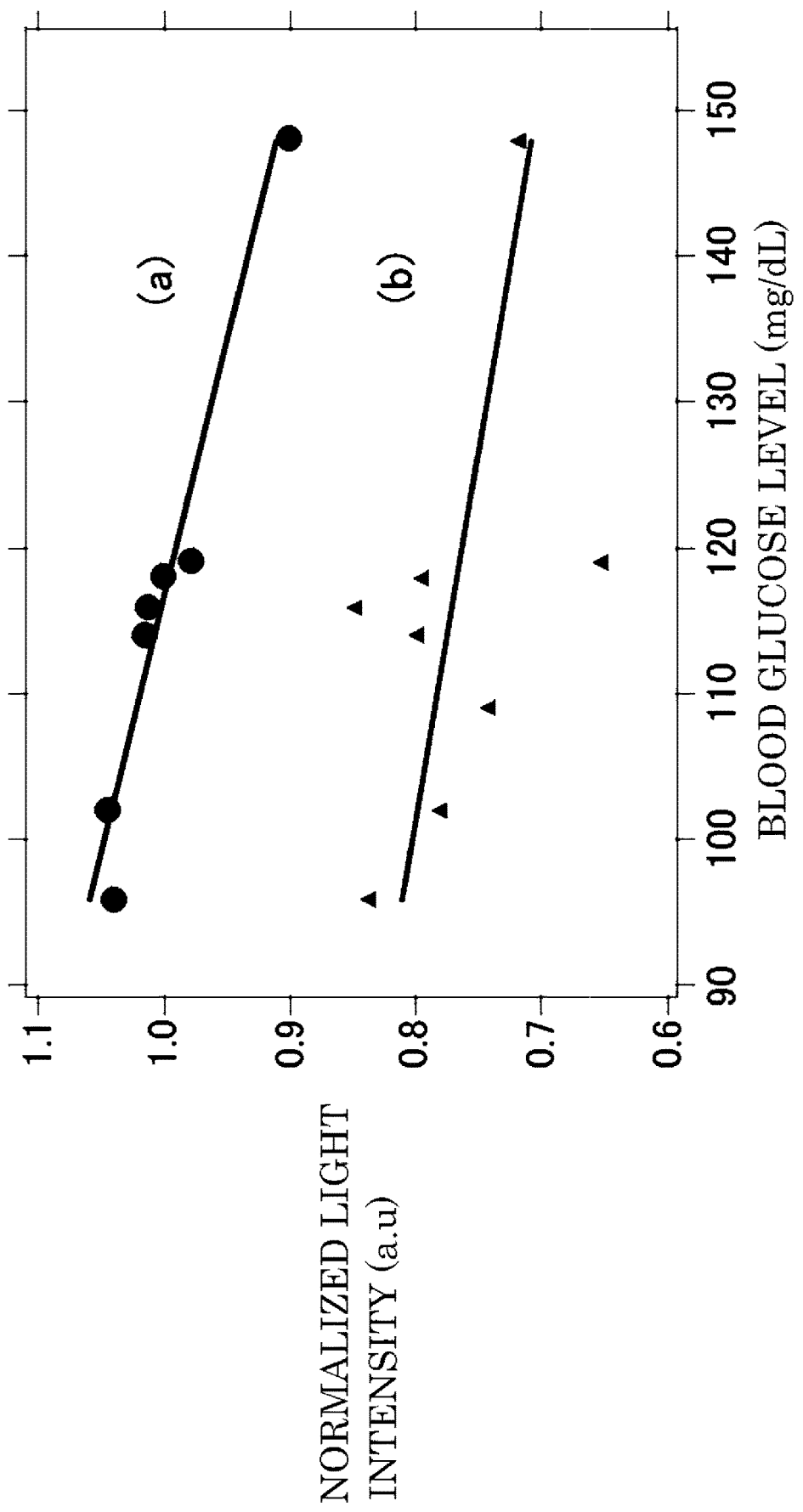
FIG. 4 illustrates the correspondence between normalized light intensity and actual blood glucose level using a blood glucose meter of an embodiment of the present invention, and illustrates measurement results for (a) the case in which a light guiding section and window are used, and (b) the case in which these are not used.

FIG. 4 illustrates the results when, after orally ingesting an aqueous solution in which 37 g of glucose is dissolved in approximately 200 ml of water, the blood glucose level is measured using an invasive blood glucose level measurement method on the same body, and the results when correspondence between the signal ratio of the light detector 40 and the monitoring light detector 16 in the configuration described above (normalized light intensity) is measured for different blood glucose levels. A Q-switched Nd:YAG laser is used as the excitation light source 11. Here, (a) in FIG. 4 illustrates the results when the configuration in FIGS. 1 and 3 is used, and (b) in FIG. 4 illustrates the results when laser light 100 having the same angle of incidence directly enters into the body epithelium F. Here, it is presumed that the blood glucose level that is measured using an invasive blood glucose level measurement method represents the true blood glucose level. The number of irradiations of the laser light 100 is 256 shots per time, and the measurement time is approximately 30 seconds.

In both (a) and (b) in FIG. 4, the normalized light intensity decreases as the blood glucose level increases. This is caused by laser light 100 having a wavelength of 9.26 µm being absorbed by glucose in the epithelial interstitial fluid. However, when compared with the regression line, in the case of (b) there is variation of about ±10.3%, and in the case of (a), this variation decreases to a level that can be ignored in the figure (about ±2%). Therefore, particularly in the case of (a) there is a 1-to-1 correspondence between the light intensity that is measured by the light detector 40 and the true blood glucose level, and it is possible to find the true blood glucose level on a 1-to-1 basis from just the light intensity that is measured by the light detector 40. Consequently, complicated statistical analysis and the like is not needed, and with the simple device configuration illustrated in FIG. 1, it is possible to measure the glucose concentration in blood (blood glucose level).

In the example above, during the approximate 30 seconds required for one measurement, it is not always easy to stably bring the body epithelium F in contact with the window 30, and in some cases it is difficult for the first test subject to perform measurement with good accuracy. Therefore, a Q-switched Nd:YAG laser that is able to emit a pulse-like excitation light having a wavelength of 1.064 µm at a repetition of 100 Hz is used as the excitation light source 11, and the blood glucose levels for plural test subjects was measured. In this case, the number of irradiations of laser light is 256 shots per time, however, the repetition number of laser is 100 Hz, so the measurement time is greatly shortened to about 3 seconds. Furthermore, in this case, an electron-cooled HgCdTe detector that does not require liquid-nitrogen cooling having, however has an inferior S/N ratio when compared with the case of a liquid-nitrogen cooling is used as the light detector 40 and the monitoring light detector 16. The other configuration is the same as in the example described above.

Figure 5:
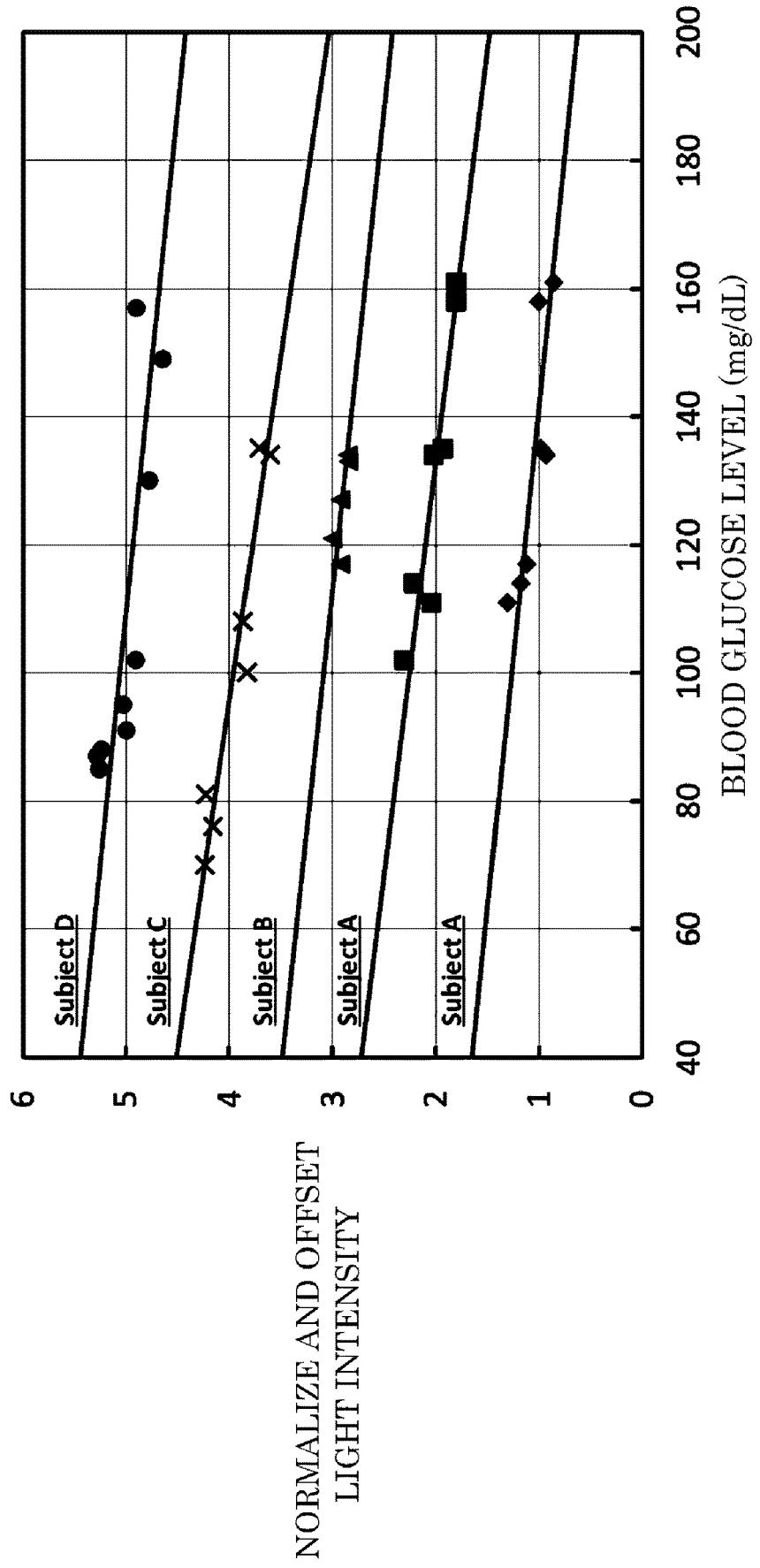
FIG. 5 illustrates the correlation between the normalized light intensity and actual blood glucose levels obtained using a blood glucose meter of an embodiment of the present invention for three test subjects using a high number of repetitions of laser light.

An aqueous solution in which 37 g of glucose is dissolved in approximately 200 ml of water is orally ingested by test subjects (healthy persons), after which an oral glucose tolerance test (OGTT) for examining the blood glucose level is performed for test subjects A, B, C and D. FIG. 5 illustrates the correlation of the result of measuring the blood glucose level at this time using a blood collection type blood glucose level measurement method, and signal ratio (normalized light intensity) of the monitoring light detector 16 and light detector 40 of the configuration described above that is measured for different blood glucose levels.

In FIG. 5, the normalized light intensity decreases as the blood glucose level increases. The accuracy of the error by comparison with the invasive blood glucose level measurement method is ±9% (bottom) and ±6% (top) for test subject A, and ±5.5%, ±12.5% and ±19.5% for test subjects B, C and D, respectively. These values all satisfy the ISO standard for measurement accuracy of ±20% or less, and data that is comparable to that of commercially available invasive blood glucose level measurement devices is obtained. In this case, measurement is completed with the amount of time for one irradiation being only about 3 seconds, so it is not necessary to devise a special device for stably bringing the body epithelium F in contact with the window 30, and it is possible for even a first time subject to measure the glucose level with accuracy equal to or better than a commercially available blood glucose level measurement device. Furthermore, the glucose level can be measured easily and in a much shorter time than with an invasive blood glucose level measurement device, making it possible to greatly reduce a patient's stress. In this way, preferably the repetition frequency of laser light 100 is high, and a frequency of 1 Hz or greater is preferred.

Moreover, actually the light intensity of the diffused reflected light 200 (wavelength $\lambda_1$) is also affected by factors other than glucose such as the absorption of incident light by the skin, or components other than glucose in the interstitial fluid. By setting the wavelength to $\lambda_1$ at which the absorption due to glucose is especially large, it is possible to reduce the effect of absorption due to factors other then glucose. Furthermore, by obtaining the characteristics in FIG. 4 beforehand for the same subject when the effect of absorption due to factors other than glucose does not fluctuate over time, the fluctuation over time of the blood glucose level can be accurately calculated. Alternatively, by obtaining the characteristics in FIG. 4 according to race, gender, age and the like even when the test subjects are not the same, it is possible to increase the accuracy of measuring the blood glucose level.

Figure 6:
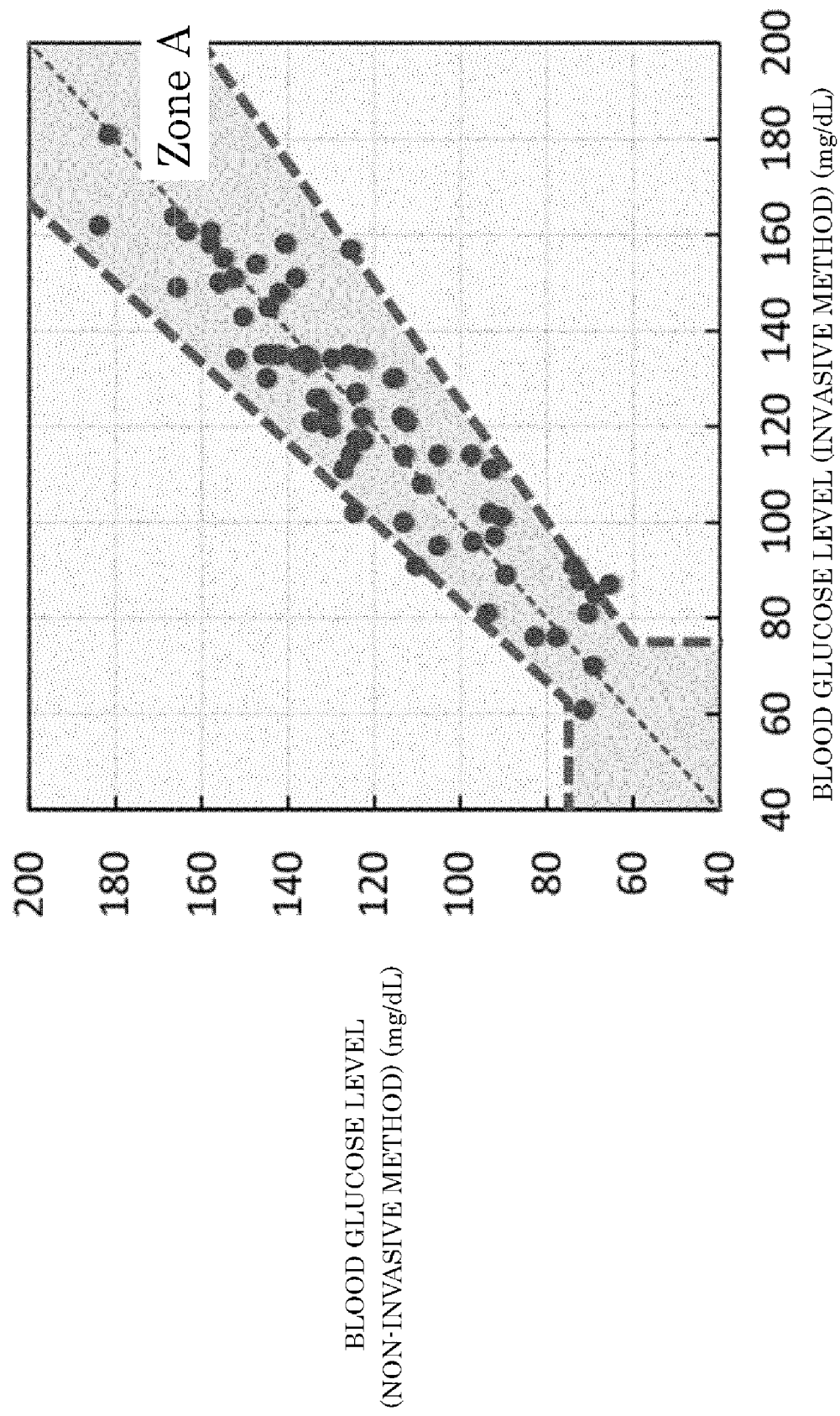
FIG. 6 illustrates the results of much data of performing a comparison between blood glucose levels obtained by collecting blood sample, and blood glucose levels obtained by using the blood glucose meter of an embodiment of the present invention.

The OGTT described above was performed on four healthy persons (A to D) multiple times on different days, and the blood glucose level was measured using an invasive method (blood sampling), while at the same time, using the normalized light intensity that is obtained by the method described above, the blood glucose level was calculated from the approximation straight line in FIG. 5. By this, a comparison of the blood glucose level obtained by blood sampling and the blood glucose level obtained by the method described above (non-invasive method) was performed for much data, and the results are shown in FIG. 6.

Actually, the blood glucose value sensor is used for medical practice, and in this case, the allowed measurement tolerance differs according to the absolute value of the actual blood glucose value. In other words, when the absolute value of the blood glucose value is small (when the subject is recognized as being healthy), and when the absolute value of the blood glucose value is large (when treatment is necessary), the allowable measurement tolerance differs. Taking this aspect into consideration, typically for the blood glucose value sensor evaluation, Clarke error grid analysis that mainly focuses on the effect that the tolerance of the measurement results have on the appropriateness of the medical treatment for a patient is used (Clarke W L, Cox D, Gonder-Frederick L A, Carter W, Pohl S L, "Evaluating Clinical Accuracy of Systems for Self-Monitoring of Blood Glucose", Diabetes Care, Vol. 10, p 622 to 628 (1987)). In Clarke error grid analysis, a correlation diagram as illustrated in FIG. 6 is such that the range recognized as being accurate measurement is set as zone A (the most preferred range).

Zone A is within ±15 mg/dl when the blood glucose value is less than 75 mg/dl, and is within ±20% when the blood glucose value is equal to or greater than 75 mg/dl. From the results in FIG. 6, a large portion of the measurement points (95% or greater) are inside zone A, and all of the measurement points other than that also exist very close to the boundary of zone A. In other words, by using the normalized light intensity as described above, it is possible to measure the blood glucose level with clinically sufficient accuracy.

In the example above, a monitoring light detector 16 is used together with a light detector 40, and the blood glucose level is calculated using the normalized light intensity of the diffused reflected light 200, however, when the stability of the laser light 100 is high, or when it is possible to monitor fluctuation of the laser light 100 by using another method, the monitoring light detector 16 and the beam splitter 15 are not necessary. In that case, instead of the normalized light intensity, it is possible to use the detection intensity (output) of the light detector 40. Alternatively, it is possible to calculate a correction factor according to the fluctuation of the laser light 100 that is monitored by another method, and use that correction factor instead of the light intensity that is detected by the monitoring light detector 16.

However, by also taking into consideration the effect of absorption due to factors other than glucose, it is possible to further increase the measurement accuracy for measuring the blood glucose level. In order for that, using a laser light having two kinds of wavelength as the laser light 100 is effective. This point will be explained below.

In the measurement described above, the wavelength of the laser light 100 is set to 9.26 μm at which a large amount of absorption due to glucose is observed. In this way, it is possible to use a laser light 100 (first laser light) having wavelength $\lambda_1$ for which the absorption due to glucose is large together with a laser light 100 (second laser light) having a wavelength $\lambda_2$ for which there is hardly any effect of absorption due to glucose. In other words, it is possible to use laser light having two wavelengths as the laser light 100.

Figure 7:
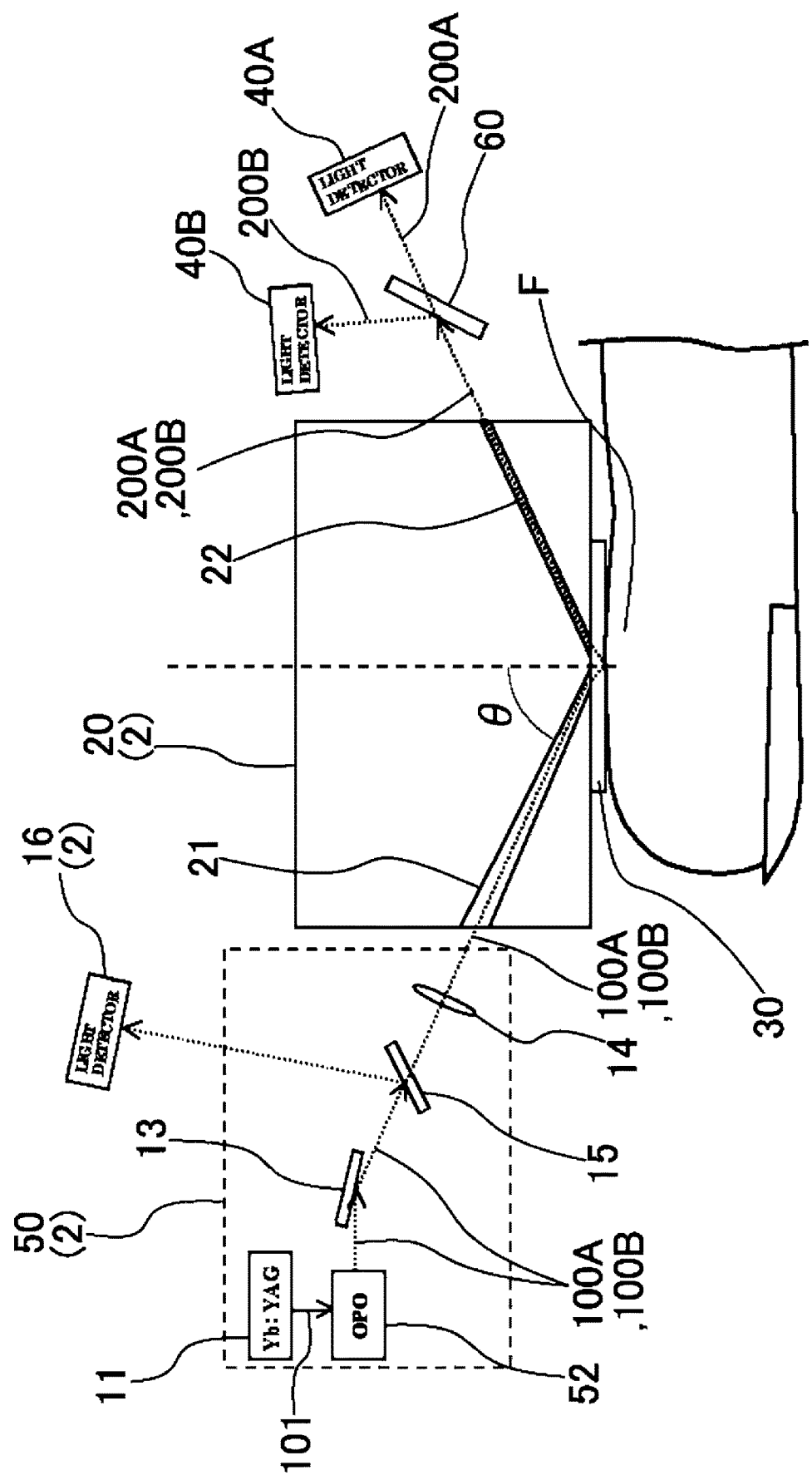
FIG. 7 illustrates the configuration of a variation of a blood glucose meter of an embodiment of the present invention.

The configuration of a blood glucose meter 2 for the case in which two wavelengths are used in this way is illustrated in FIG. 7 that is correlated with FIG. 1. In this blood glucose meter 2 as well, a light-guiding unit 20 and window that are used in the blood glucose meter 1 are used in the same way. However, the light source 50 that is used here and the configuration for detecting the light intensity of the diffused reflected light are different. In the light source 50, an excitation light source 11, mirror 13, condenser lens 14 and beam splitter 15 are used in the same way, the monitoring light detector 16 is also used in the same way.

Figure 8:
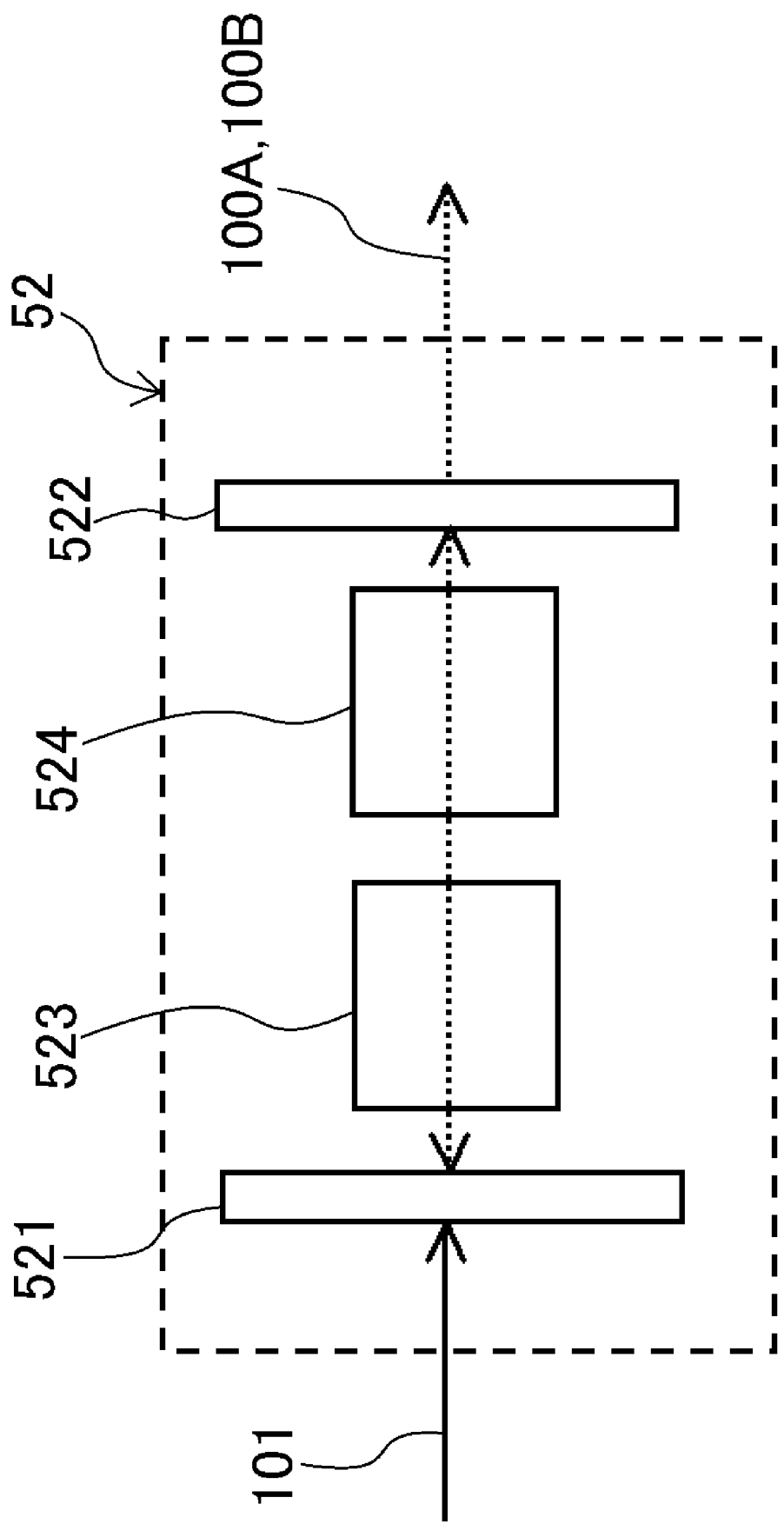
FIG. 8 illustrates an optical parametric oscillator that is used in a variation of a blood glucose level of an embodiment of the present invention.

FIG. 8 is a figure that correlates the configuration of the OPO 52 that is used here with FIG. 2. In this case, a non-linear optical crystal (first non-linear optical crystal) 523, and a different non-linear optical crystal (second non-linear optical crystal) 524 are provided between an incident side half mirror 521 and an exit side half mirror 522. Here, by using a single excitation light 101, a first laser light 100A having a wavelength λ1 is oscillated by the non-linear optical crystal 523, and simultaneously, a second laser light 100B having a wavelength λ2 is oscillated by the non-linear optical crystal 524. The first laser light 100A and the second laser light 100B are incident on the body epithelium F by way of the same optical path, and respectively corresponding first diffused reflected light 200A and second diffused reflected light 200B are emitted from a light-guiding unit 20 (exit side optical waveguide 22) by way of the same optical path.

In this configuration, it is possible to oscillate laser lights having two wavelengths using a single light source 50. When doing this, it is not necessary to perform optical-axis alignment that requires high-precision adjustment for each wavelength, and it is possible to use both the first laser light 100A and the second laser light 100B with the same optical path. In other words, by using an optical parametric oscillator for the light source, using a light-guiding unit 20 or the like for laser light of two wavelengths is particularly easy to perform. When doing this, it is possible to increase the light intensity of both the first laser light 100A and the second laser light 100B.

Here, the emitted light enters into a wavelength selection beam splitter 60 that is a half mirror. The wavelength selection beam splitter 60 is a half mirror the surface of which is coated for allowing light within a specific wavelength range to pass through, and can be set so that the first diffused reflected light 200A having a wavelength $\lambda_1$ passes through the wavelength selection beam splitter 60 and the second diffused reflected light 200A having a wavelength $\lambda_2$ is reflected by the wavelength selection beam splitter 60. Therefore, by installing a light detector (first light detection unit) 40A on this optical path for transmitted light, and installing a light detector (second light detection unit) 40B on this optical path for reflected light, the light detector 40A is able to detect the light intensity of the first diffused reflected light 200A, and the light detector 40B is able to detect the light intensity of the second diffused reflected light 200B. It is also possible to reverse the transmission and reflection relationship of the first diffused reflected light 200A and the second diffused reflected light 200B in the wavelength selection beam splitter 60.

Figure 9A:
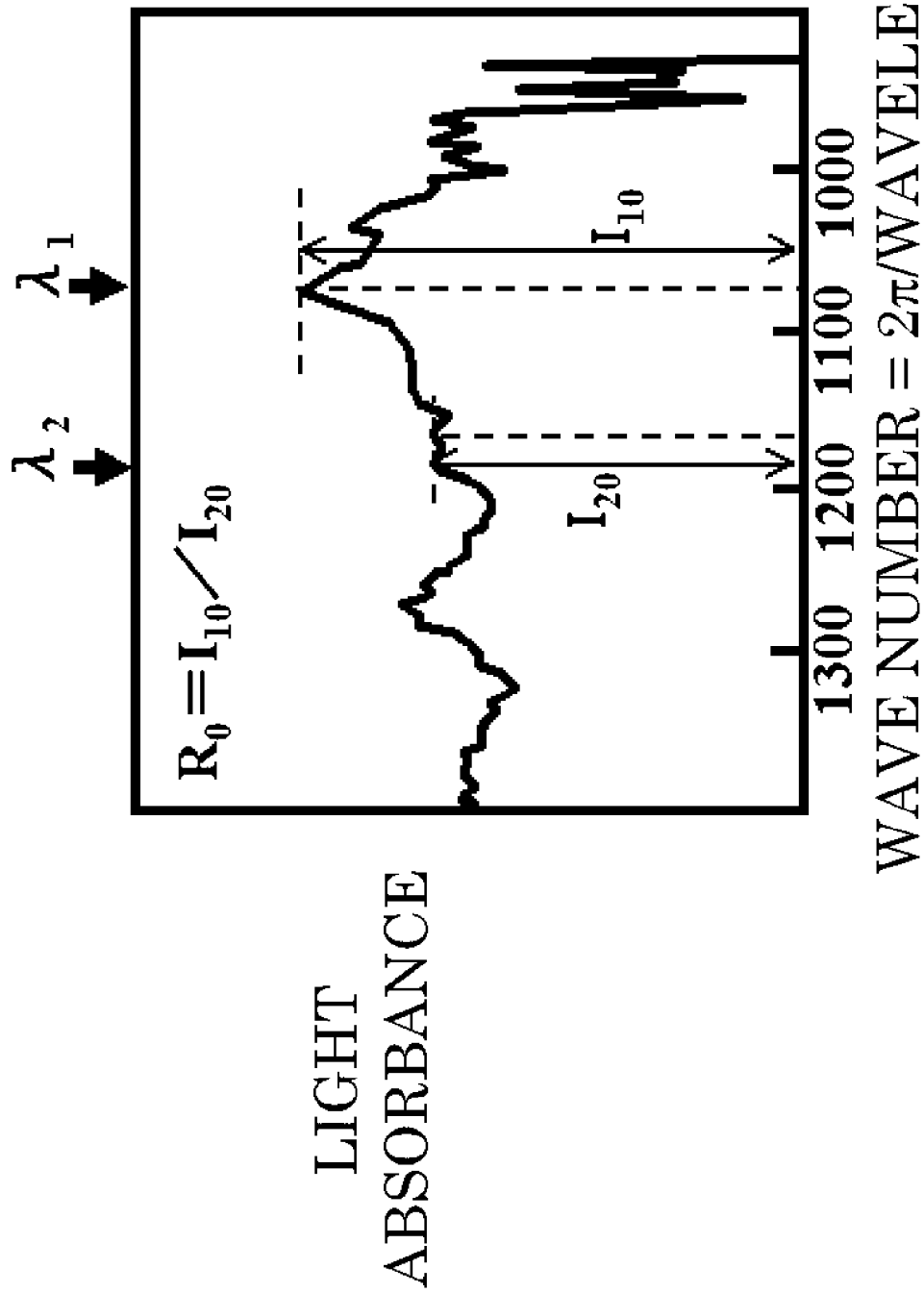
Figure 9B:
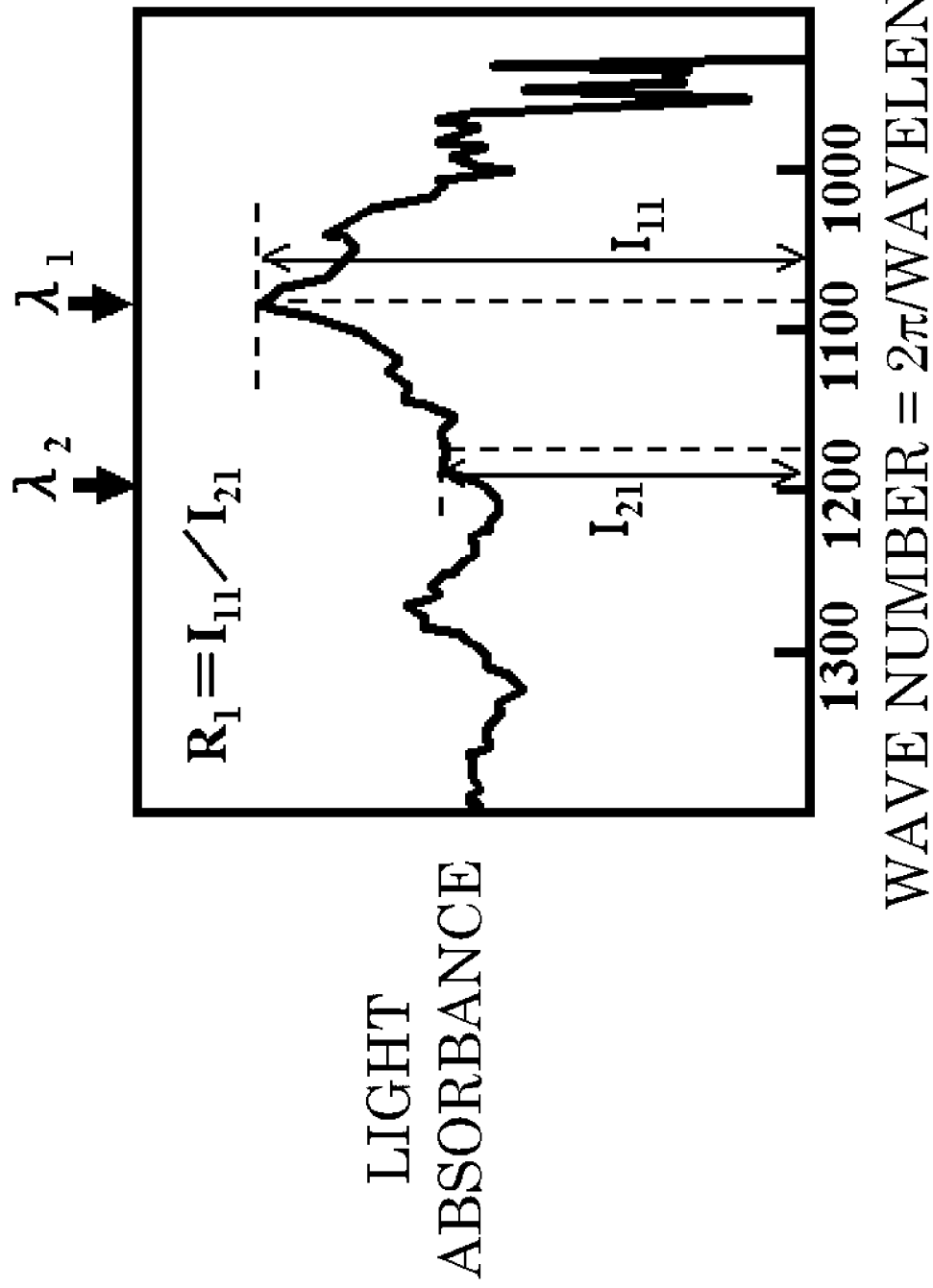

The method for calculating the blood glucose level in this case will be explained below. FIG. 9A, FIG. 9B and FIG. 9C schematically illustrate the relationship (light absorption spectrum) between the light absorption and the wavenumber (=2π/wavelength) for three kinds of glucose concentrations, with the glucose concentration becoming higher going from FIG. 9A to FIG. 9C. Here, the light absorption at a wavelength λ corresponds to (the light intensity of the incident light having wavelength λ—the light intensity of transmitted light having wavelength λ)/(light intensity of incident light having wavelength λ), the incident light corresponds to the laser light (first laser light 100A, second laser light 100B), and the transmitted light corresponds to the diffused reflected light (first diffused reflected light 200A, second diffused reflected light 200B). Therefore, when the light intensity of the laser light is fixed, the light absorption can be uniquely calculated from the intensity of diffused reflected light. Wavelength $\lambda_1$ is a wavelength having large absorption due to glucose in the same way as described above, and as described above is taken to be 9.26 μm, for example. However, wavelength $\lambda_2$ is a wavelength that on the contrary has absorption due to glucose that is small enough to be ignorable, and for example, is taken to be 8.47 μm. These wavelengths λ1, λ2 can be set by referencing the FTIR measurement spectrum described in Non-patent Document 1. When the glucose concentration is the lowest (FIG. 9A), the light absorption of wavelength $\lambda_1$ is taken to be $I_{10}$, and the light absorption of wavelength $\lambda_2$ is taken to be $I_{20}$, and when the glucose concentration is higher than this (FIG. 9B), the light absorption of wavelength $\lambda_1$ is taken to be $I_{11}$, and the light absorption of wavelength $\lambda_2$ is taken to be $I_{21}$, and when the glucose level is taken to be the highest (FIG.

9C), the light absorption of wavelength $\lambda_1$ is taken to be $I_{12}$, and the light absorption of wavelength $\lambda_2$ is taken to be $I_{22}$. The characteristics in FIG. 4 and FIG. 5 correspond to the relationship between the light absorption and the blood glucose level of wavelength $\lambda_1$.

Figure 10:
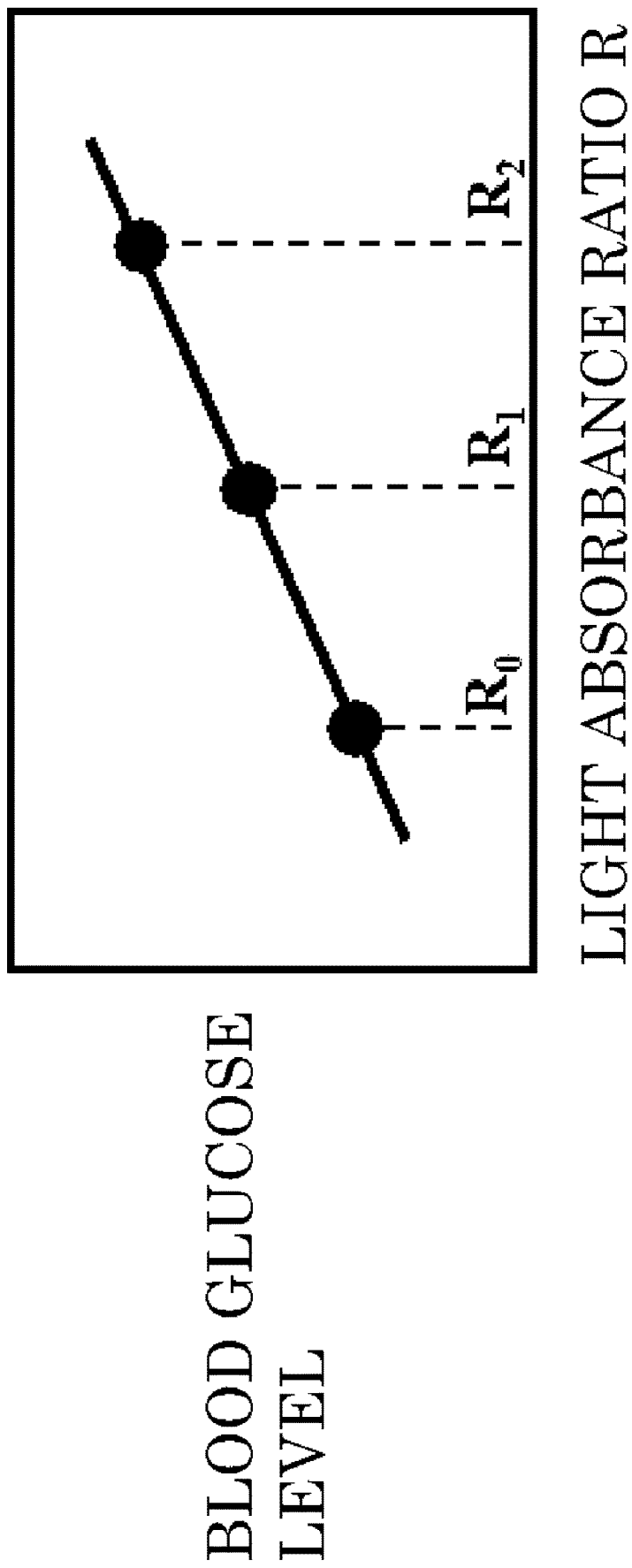
FIG. 10 is an example that schematically illustrates the relationship between the absorption and the blood glucose level.

Here, the effect of absorption due to factors other than glucose appears in both the light absorption of wavelength $\lambda_1$ and the light absorption of wavelength $\lambda_2$. Therefore, instead of the normalized light intensity in FIG. 4, as illustrated in FIGS. 9A to 9C, a light absorption ratio R=(light absorption $I_1$ of wavelength $\lambda_1$)/(light absorption $I_2$ of wavelength $\lambda_2$) is used, and by using this absorption ratio R instead of the normalized light intensity (light intensity of wavelength $\lambda_1$) in FIG. 4, it possible to calculate the blood glucose level with high accuracy even when it is not possible to ignore the effects of absorption due to factors other than glucose. In this case, it is possible to use $R_0$, $R_1$ and $R_2$ illustrated in FIGS. 9A to 9C as the light absorption ratio R, so by measuring $R_0$, $R_1$ and $R_2$ and finding the blood glucose levels corresponding to these ratios by an invasive method beforehand, it is possible to find the relationship between R and the blood glucose level such as illustrated in FIG. 10. As a result, after that, the light absorption of wavelength $\lambda_1$ is calculated from the light intensity of diffused reflected light 200 of wavelength $\lambda_1$, and the light absorption of wavelength $\lambda_2$ is calculated from the light intensity of diffused reflected light 200 of wavelength $\lambda_2$, and by finding the light absorption ratio R, it is possible to calculate the blood glucose level from the characteristics in FIG. 10. From this, it is possible, for example, to accurately calculate the blood glucose level regardless of race, gender, age and the like.

In this way, it is possible to calculate the blood glucose level as described above by using the light intensity of the first diffused reflected light 200A that is detected by the light detector 40A, and the light intensity of the second diffused reflected light 200B that is detected by the light detector 40B. However, in this case as well, it is possible to perform even more precise measurement by using a light intensity that is obtained by normalizing the light intensity of the first diffused reflected light 200A that is detected by the light detector 40 by the light intensity of the first laser light 100A or second laser light 100B that is detected by the monitoring light detector 16 instead of the light intensity of the first diffused reflected light 200A that is detected by the light detector 40A. In that case, depending on the setting of the beam splitter 15, it is possible to set the monitoring light detector 16 to detect either the first laser light 100A or the second laser light 100B. Both the first laser light 100A and the second laser light 100B are oscillated by using a single OPO 52, so for monitoring (normalizing) the light intensity, either the first laser light 100A or the second laser light 100B can be set to be detected by the monitoring light detector 16. Alternatively, as in the case of diffused reflected light, the calculation described above can be performed by dividing the monitored laser light by a wavelength selection beam splitter, and using light intensity that is normalized for each wavelength by using a monitoring light detector for each wavelength.

In the configuration described above, a first laser light 100A and a second laser light 100B having different wavelengths were simultaneously oscillated from a single light source 50 and used. After that, a first diffused reflected light 200A and a second diffused reflected light 200B that are respectively obtained from each of these are divided by using a wavelength selection beam splitter 60, and each is respectively detected by a light detector 40A and 40B. However, for example, configuration can also be such that the first laser light 100A and second laser light 100B pass through a rotatable wavelength selection filter before entering into the incident side optical waveguide. In that case, the wavelength that passes through the wavelength selection filter can be set to either $\lambda_1$ or $\lambda_2$ according to the set angle (rotation angle) of the wavelength selection filter, and when the wavelength selection filter is rotated, the first laser light 100A or second laser light 100B is alternately incident on the body epithelium, and according to this, the first diffused reflected light 200A and the second diffused reflected light 200B are alternately switched and outputted. In this case, the wavelength selection beam splitter 15 described above is not necessary, and as in the configuration illustrated in FIG. 1, it is possible to respectively detect the light intensity of the first diffused reflected light 200A and the second diffused reflected light 200B by using a single light detector 40, and the blood glucose level can be calculated in the same way as described above. In this case, it is not possible to detect the first diffused reflected light 200A and the second diffused reflected light 200B at the same time, however, by increasing the speed of rotation of the wavelength selection filter, the lag between the detection timing for detecting the first diffused reflected light 200A and the second diffused reflected light 200B can be made to be on the order of a millisecond for example. When the rate of change over time of the blood glucose level is taken into consideration, the degree of this lag is ignorable.

The wavelength $\lambda_1$ having large absorption by glucose can be appropriately selected from an absorption spectrum, and $\lambda_1$ can be set from within the range of approximately 7 μm to approximately 11 μm, and preferably from within the range of approximately 9.0 μm to approximately 9.5 μm (9.26 μm in the example described above). On the other hand, wavelength $\lambda_2$ that has small absorption by glucose, can also be set in the same way, and in the example described above $\lambda_2 < \lambda_1$, however $\lambda_2 > \lambda_1$ is also possible. The second laser light 100B is used as a reference, so preferably a wavelength having a large difference in absorption by glucose when compared with the wavelength $\lambda_1$ is set as $\lambda_2$. $\lambda_1$ and $\lambda_2$ are preferably both set from a range of wavelengths 2.5 to 12 μm in the mid-infrared region that can be emitted with high output by an optical parametric oscillator.

As described above, when using only one wavelength $\lambda_1$, and also when using two wavelengths $\lambda_1$ and $\lambda_2$, there is no need for spectrum measurement such as described in Non-patent Document 1 or Patent Document 3. Moreover, there is also no need for complex processing such as multivariate analysis. The calculation of the blood glucose level is obtained for each pulse of the laser light 100 (first laser light 100A, second laser light 100B). Therefore, after obtaining many measurement results for each of many pulses by increasing the repetition frequency of the laser light 100, statistical analysis of the blood glucose levels that are calculated for each pulse is performed, and by doing so it is possible to further increase the measurement accuracy of the blood glucose level.

The repetition frequency of the laser light 100 is determined by the repetition frequency of the excitation light source 11. In a case such as this, using a passive Q-switched Yb:YAG laser or a passive Q-switched Nd:YAG laser (Q-switched Nd:YAG laser) is preferred, and particularly, using a Q-switched Yb:YAG laser is preferred. Preferably this repetition frequency is 1 Hz or greater, and a repetition frequency of approximately 5 Hz to approximately 1 kHz that makes it possible to complete measurement in a short period of time is preferred, and particularly using a repetition frequency of approximately 10 Hz to approximately 100 Hz is preferred.

As was described above, what is actually measured by the blood glucose meter or the blood glucose level measurement method described above is the glucose concentration in the epithelial interstitial fluid. In this case, absorption is large so using mid-infrared light that does not penetrate deep into the body, and that makes it possible to precisely measure absorption due to the hydroxyl group of glucose is particularly preferred. When doing this, when the incident angle θ that is based on the normal direction in FIG. 1 and FIG. 7 is small, light enters more deeply from the epidermis and absorption by glucose in the interstitial fluid becomes larger, however, absorption by water also becomes large, so the intensity of the diffused reflected light that is to be detected decreases. Conversely, when θ is large, light does not enter deep into the body, however, also conversely, the light does not sufficiently reach the epithelial interstitial fluid, and it becomes difficult to grasp the change in absorption due to glucose. Therefore, from the aspect of measuring the blood glucose level, there is a preferred range for θ. As a result, it is necessary to precisely control the incident angle θ. In a case such as this, as described above this incident angle is strictly controlled by using a waveguide in which an incident side optical waveguide 21 and exit side optical waveguide 22 are provided.

Figure 11:
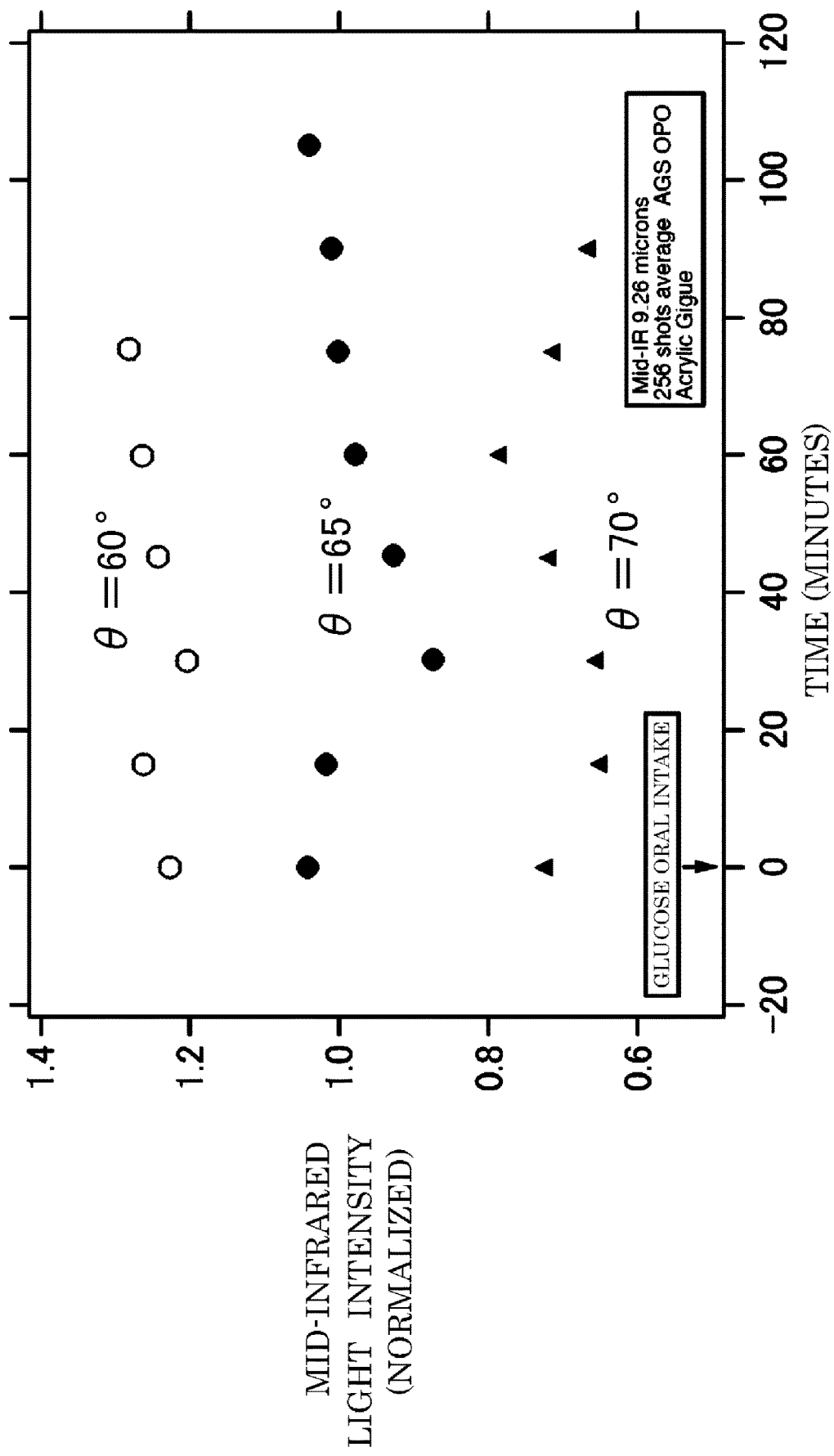
FIG. 11 illustrates measurement results for the change over time of the light intensity of diffused reflected light for three kinds of incident angles of laser light after ingestion of glucose by a test subject.

FIG. 11 illustrates the results of measuring the change over time of the output of the light detector 40 in the case of a wavelength $\lambda_1=9.26$ μm that is detected when the incident angle θ based on the normal direction in FIG. 1 is 60°, 65° and 70° after the ingestion of glucose by the test subject. As θ increases, the depth of penetration of the laser light 100 becomes shallower, and values nearer the skin are measured.

Figure 12:
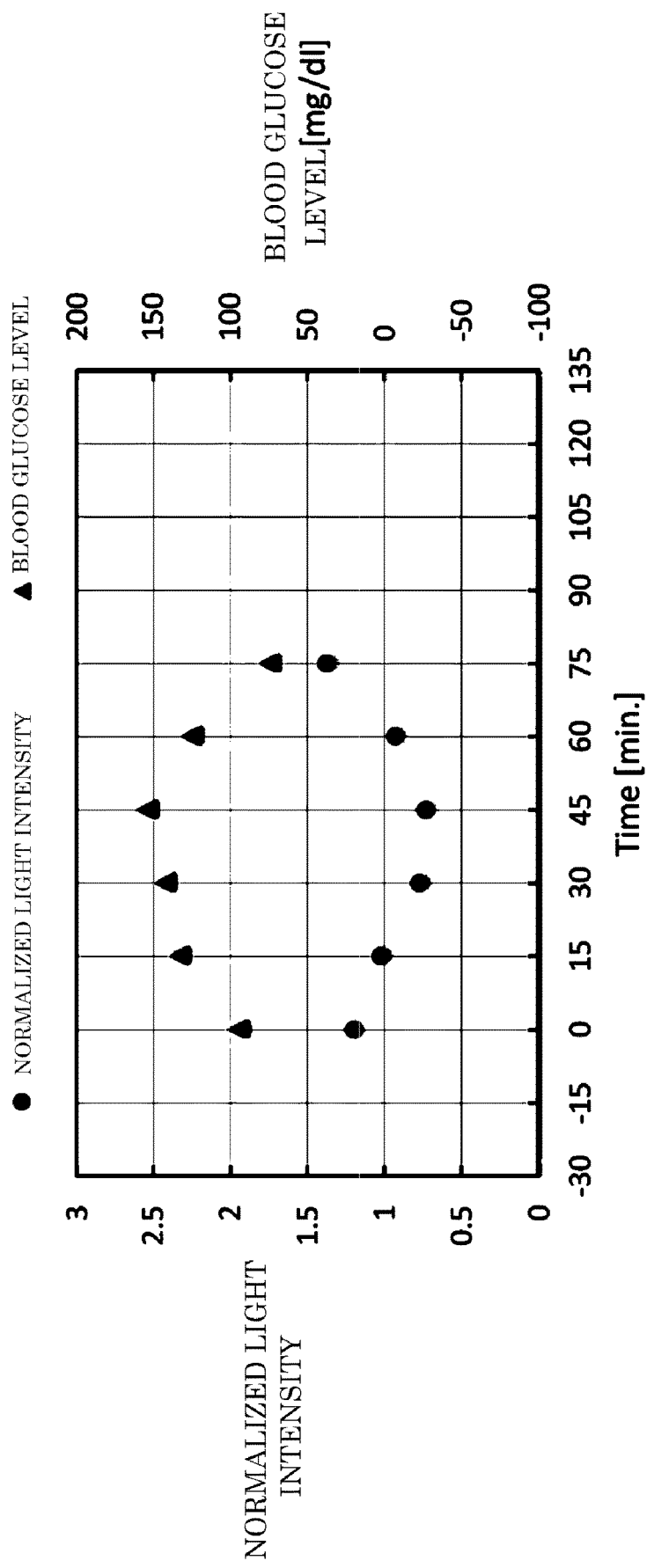
FIG. 12 is an example of the change over time of the blood glucose level after eating that is measured invasively.

Moreover, FIG. 12 illustrates the value of the blood glucose level over time of a healthy person A after eating that is measured by an invasive method (measured by blood sampling), and the output intensity (normalized by the input intensity) over time of the output of the light detector 40 that is measured by the method described above with θ=65.5°. It is known that typically after eating the blood glucose level rises temporarily, then after that decreases, and the change in the blood glucose level in FIG. 12 changes in this way. When the blood glucose level increases, absorption by glucose becomes large, so the output intensity decreases. From the results in FIG. 12 it is clearly seen that the change in the blood glucose level measured by an invasive method corresponds to this change in the output intensity.

From the results above, when θ is at least in the range of approximately 60° to approximately 70°, the absolute value of the output of the light detector 40 differs, however, a change in the glucose concentration is confirmed, and when θ=65°, it is particularly possible to definitely confirm that the glucose concentration decreases after ingestion. Therefore, the glucose concentration that is recognized at least when θ=65° is the glucose concentration in the subcutaneous interstitial fluid at a depth that corresponds to when θ=65°, however, it can be estimated as being close to the original blood glucose level that is to be measured. In FIG. 11, the output of the light detector 40 is illustrated for each θ, and by calculating the characteristics in FIG. 4 beforehand for each θ, it is possible to be converted to the glucose concentration. As described above, θ is determined according to the construction of the light-guiding unit 20. However, even when a incident-side optical waveguide 21 is not used, as long as it is possible to irradiate laser light 100 having sufficient light intensity on the body epithelium F at an incident angle θ, there is no need to provide an incident side optical waveguide in the light-guiding unit. FIG. 11 illustrates data for θ=60°, 65° and 70°, however, measurement is possible with θ being in a range of at least 35° to 85°.

In the example described above, a case was explained for measuring the blood glucose level (glucose concentration in the blood), however, it is also possible to perform similar measurement of substance in blood such as lipids for which absorption can be measured using laser light (wavelength $\lambda_1$) in the mid-infrared region (wavelength of approximately 2.5 to approximately 12 μm) that can be oscillated using an OPO. When doing this, when a wavelength $\lambda_2$ for which absorption can be ignored can be set in the same mid-infrared region in the same way as described above, it is possible to further improve the measurement accuracy. In other words, the device for measuring the concentration of substance in blood and method for measuring the concentration of substance in blood can be applied to an arbitrary substance in blood having such characteristics. When doing this, the non-linear optical crystal or excitation light source that is used in the OPO can be selected according to the settings of $\lambda_1$ and $\lambda_2$. As long as the light source is capable of similarly oscillating pulse shaped excitation light in the OPO, the light source can be similarly used as an excitation light source. In such as case as well, it is possible to similarly use a single optical parametric oscillator in which two non-linear optical crystals are arranged, so the configuration of the entire measuring apparatus can be simplified. Moreover, similarly there is no need to use a complex analysis method.

Furthermore, it is possible to use a carbon dioxide gas ($CO_2$) laser oscillator as the light source that has the same wavelength as the light source 10, 50 described above, and that is similarly capable of repeated pulse shaped oscillation. As is well known, a $CO_2$ laser oscillator oscillates laser light having a wavelength that can be adjusted within the range 9.1 to 10.8 μm according to the setting of the vibration level in transition that contributes to light emission. Therefore, by taking the wavelength $\lambda_1$ that has large absorption by glucose to be 9.2 μm, and the wavelength $\lambda_2$ having small absorption by glucose to be 10.2 μm, for example, it is also possible to alternately oscillate laser light of wavelengths $\lambda_1$ and $\lambda_2$.

Moreover, when a $CO_2$ laser oscillator is used, by using a high-speed semiconductor switching element, it is possible to repeatedly oscillate laser light having a pulse width of 10 to 50 ns and a rising time and falling time of 10 ns at 1 Hz or greater. When doing this, the spire output of the pulse can be taken to be 10 W to 1 kW. Therefore, it is possible to use a $CO_2$ laser oscillator instead of the light sources 10, 50 described above.

DESCRIPTION OF REFERENCE NUMBERS 1, 2 Blood glucose meter (device for measure the concentration of substance in blood)
10, 50 Light source
11 Excitation light source
12, 52 OPO (Optical parametric oscillator)
13 Mirror
14 Condenser lens
15 Beam splitter
16 Monitoring light detector (monitoring light detection unit)
20 Light-guiding unit
21 Incident-side optical waveguide
22 Exit-side optical waveguide 30 Window
30A Slit
40 Light detector (light detection unit)
40A Light detector (first light detection unit)
40B Light detector (second light detection unit)
60 Wavelength selection beam splitter
100 Laser light
100A First laser light
100B Second laser light
121, 521 Incident side half mirror
122, 522 Exit side half mirror
123 Non-linear optical crystal
200 Diffused reflected light
200A First diffused reflected light
200B Second diffused reflected light
523 First non-linear optical crystal
524 Second non-linear optical crystal
F Body epithelium (Body)

What is claimed is:

1. A device for measuring a concentration of substance in blood that measures the concentration of the substance that is included in the blood of a body, comprising:
a laser oscillator that oscillates a first laser light having a wavelength that is within the range 2.5 μm to 12 μm, and that is absorbed by the substance;
a light-guiding unit that guides the first laser light to the body, and guides first diffused reflected light that is generated by the first laser light from the body; and
a light-detection unit that detects a light intensity of the first diffused reflected light,
the light-guiding unit comprising: an incident-side optical waveguide that is configured to guide the first laser light to the body; and an exit-side optical waveguide that guides the first diffused reflected light to the light-detection unit,
on a cross section of the light-guiding unit, the incident-side optical waveguide and the exit-side optical waveguide being provided to form a substantially V shape.

2. The device for measuring the concentration of substance in blood according to claim 1, wherein
the light-guiding unit guides the first laser light to the body at an incident angle of 35° to 85°.

3. The device for measuring the concentration of substance in blood according to claim 1, wherein
the laser oscillator
is an optical parametric oscillator that uses excitation light having a wavelength that is different than the first laser light and that is emitted from an excitation light source, and that oscillates the first laser light by a first non-linear optical crystal.

4. The device for measuring the concentration of substance in blood according to claim 3, wherein
the excitation-light source is a passive Q-switched Nd:YAG laser or passive Q-switched Yb:YAG laser.

5. The device for measuring the concentration of substance in blood according to claim 4, wherein
the excitation-light source oscillates a pulsed excitation light with a repetition frequency of 1 Hz or greater.

6. The device for measuring the concentration of substance in blood according to claim 1, wherein
the laser oscillator is a carbon dioxide gas laser oscillator.

7. The device for measuring the concentration of substance in blood according to claim 6, wherein
the laser oscillator oscillates a second laser light having a wavelength within the range 2.5 to 12 μm and that is different than that of the first laser light, and that has a characteristic of being absorbed by the substance less than the first laser light; and
in the light-guiding unit
the incident-side optical waveguide is configured to guide the second laser light to the body, and the exit-side optical waveguide guides second diffused reflected light that is generated by the second laser light to the light-detection unit.

8. The device for measuring the concentration of substance in blood according to claim 7, wherein
the laser oscillator oscillates the first laser light and the second laser light in a pulsed shape with a repetition frequency of 1 Hz or greater.

9. The device for measuring the concentration of substance in blood according to claim 1, wherein
the substance is glucose; and
the wavelength of the first laser light is within the range 7.0 μm to 11 μm.

10. A device for measuring a concentration of substance in blood that measures the concentration of the substance that is included in the blood of a body, comprising:
a laser oscillator that oscillates a first laser light having a wavelength that is within the range 2.5 μm to 12 μm, and that is absorbed by the substance;
a light-guiding unit that guides the first laser light to the body, and guides first diffused reflected light that is generated by the first laser light from the body; and
a light-detection unit that detects a light intensity of the first diffused reflected light, wherein
the light-guiding unit comprises:
an incident-side optical waveguide that guides the first laser light to the body; and
an exit-side optical waveguide that guides the first diffused reflected light to the light-detection unit;
the laser oscillator is an optical parametric oscillator that uses excitation light having a wavelength that is different than the first laser light and that is emitted from an excitation light source, and that oscillates the first laser light by a first non-linear optical crystal;
the laser oscillator oscillates a second laser light having a wavelength that is within the range 2.5 to 12 μm and that is different than that of the first laser light, and that has a characteristic of being absorbed by the substance less than the first laser light; and
in the light-guiding unit
the incident-side optical waveguide is configured to guide the second laser light to the body, and the exit-side optical waveguide guides second diffused reflected light that is generated by the second laser light to the light-detection unit.

11. The device for measuring the concentration of substance in blood according to claim 10, wherein
the optical parametric oscillator comprises a second non-linear optical crystal that generates the second laser light using the excitation light.

12. The device for measuring the concentration of substance in blood according to claim 11, wherein
in the optical parametric oscillator, the first non-linear optical crystal and the second non-linear optical crystal are arranged in series on an optical path.

13. The device for measuring the concentration of substance in blood according to claim 10, further comprising
a window that is configured for insertion between the light-guiding unit and the body, and that is made using a material that allows the second laser light to pass through, and has a shape so that when inserted between the light-guiding unit and the body and brought in contact with the body, a space is formed between the window and the body through which the first laser light and the second laser light pass.

* * * * *